US010789711B2

(12) United States Patent
Mischi et al.

(10) Patent No.: US 10,789,711 B2
(45) Date of Patent: Sep. 29, 2020

(54) IMAGING OF DISPERSION AND VELOCITY OF CONTRAST AGENTS

(71) Applicant: TECHNISCHE UNIVERSITEIT EINDHOVEN, Eindhoven (NL)

(72) Inventors: Massimo Mischi, Eindhoven (NL); Ruud Johannes Gerardus Van Sloun, Eindhoven (NL)

(73) Assignee: TECHNISCHE UNIVERSITEIT EINDHOVEN, Eindhoven (NL)

( * ) Notice: Subject to any disclaimer, the term of this patent is extended or adjusted under 35 U.S.C. 154(b) by 383 days.

(21) Appl. No.: 15/758,845

(22) PCT Filed: Sep. 8, 2016

(86) PCT No.: PCT/EP2016/071191
§ 371 (c)(1),
(2) Date: Mar. 9, 2018

(87) PCT Pub. No.: WO2017/042280
PCT Pub. Date: Mar. 16, 2017

(65) Prior Publication Data
US 2020/0234446 A1 Jul. 23, 2020

(30) Foreign Application Priority Data

Sep. 9, 2015 (EP) .................................... 15184473
May 27, 2016 (EP) .................................... 16171625

(51) Int. Cl.
*G06T 7/00* (2017.01)
*A61B 8/08* (2006.01)
(Continued)

(52) U.S. Cl.
CPC ............ *G06T 7/0016* (2013.01); *A61B 8/481* (2013.01); *A61B 8/5223* (2013.01); *G06T 7/246* (2017.01);
(Continued)

(58) Field of Classification Search
CPC ........... A61B 6/481; A61B 6/507; A61B 6/12; A61B 3/12; A61B 5/0059; A61B 5/411;
(Continued)

(56) References Cited

U.S. PATENT DOCUMENTS 6,217,520 B1 * 4/2001 He ........................... A61B 8/00
600/467
6,241,675 B1 * 6/2001 Smith ...................... A61B 8/06
128/916
(Continued)

OTHER PUBLICATIONS

Kuenen, M.P.J., et al., "Coherence-based Contrast Ultrasound Diffusion Imaging for Prostate Cancer Detection," 10.1109/ULTSYM. 2010.0489, 2010 IEEE International Ultrasonics Symposium Proceedings, pp. 1936-1939.
(Continued)

*Primary Examiner* — Aklilu K Woldemariam
(74) *Attorney, Agent, or Firm* — Kenealy Vaidya LLP

(57) ABSTRACT

Some embodiments are directed to a method of estimating a velocity of a contrast agent. The method includes receiving a plurality of video frames that were produced using a dynamic contrast enhanced imaging process, each video frame including a plurality of pixels/voxels. Information from the video frames is used to estimate velocity vectors indicating the velocity and direction of the agent with the vascular networks. The estimated velocity can be used to diagnose cancer, such as prostate cancer. Instead of velocity vectors, agent trajectories can be determined also used for the same purpose.

22 Claims, 12 Drawing Sheets

(51) Int. Cl.
*G16H 30/20* (2018.01)
*G16H 30/40* (2018.01)
*G16H 50/50* (2018.01)
*G16H 50/20* (2018.01)
*G06T 7/246* (2017.01)
*A61B 8/06* (2006.01)

(52) U.S. Cl.
CPC ............ *G16H 30/20* (2018.01); *G16H 30/40* (2018.01); *G16H 50/20* (2018.01); *G16H 50/50* (2018.01); *A61B 8/06* (2013.01); *A61B 8/085* (2013.01); *G06T 2207/10016* (2013.01); *G06T 2207/10096* (2013.01); *G06T 2207/10136* (2013.01); *G06T 2207/30081* (2013.01); *G06T 2207/30096* (2013.01); *G06T 2207/30104* (2013.01)

(58) Field of Classification Search
CPC ..... A61B 5/4842; A61B 5/7267; A61B 8/469; A61B 8/5223; A61B 5/743; A61B 6/032; A61B 8/481; A61B 8/5246; A61B 5/14546; G01S 7/52066; G01N 23/046; A61K 38/00; C07K 14/615; G01J 2003/1213; G01J 3/021; G01J 3/10; G01J 3/2823; G06T 2200/04; G06T 7/12; G06T 2207/10016; G06T 2207/10024; G06T 2200/24; G06T 5/40; G06T 2207/20081; G06T 7/11; G06K 9/6201; G06K 9/6218; G06K 9/00765; G16H 50/50; H04N 21/4318; H04N 5/2355; H04N 5/57; H04N 9/045; H04N 5/76; H04N 13/243; H04N 5/2625; A61P 19/02; A63F 13/53; G06F 3/011; G06N 20/10
USPC ........ 382/107, 128, 168, 294; 600/443, 458, 600/467, 476
See application file for complete search history.

(56) References Cited

U.S. PATENT DOCUMENTS

| | | | |
|---|---|---|---|
| 7,113,817 B1* | 9/2006 | Winchester, Jr. | A61B 3/1233 356/27 |
| 7,324,673 B1* | 1/2008 | Yamanaka | G06T 5/009 358/520 |
| 8,406,859 B2* | 3/2013 | Zuzak | A61B 5/0059 600/476 |
| 9,072,492 B2* | 7/2015 | Arditi | A61B 8/481 |
| 9,779,774 B1* | 10/2017 | Kang | G06K 9/6218 |
| 9,811,884 B2* | 11/2017 | Foi | H04N 5/33 |
| 10,433,817 B2* | 10/2019 | Frinking | A61B 8/06 |
| 2003/0092991 A1* | 5/2003 | Sehgal | A61B 8/543 600/458 |
| 2005/0163393 A1* | 7/2005 | Asari | G06T 5/009 382/254 |
| 2006/0034419 A1* | 2/2006 | Nishide | A61B 6/027 378/15 |
| 2008/0004904 A1* | 1/2008 | Tran | A61B 5/0022 705/2 |
| 2008/0212838 A1* | 9/2008 | Frigerio | G06T 7/269 382/107 |
| 2011/0317881 A1* | 12/2011 | Bonnefous | G06T 7/30 382/107 |
| 2012/0301967 A1* | 11/2012 | Nadkarni | G01N 33/4905 436/69 |
| 2013/0072420 A1* | 3/2013 | Skerra | A61P 5/00 514/1.1 |
| 2018/0090173 A1* | 3/2018 | Bradley | G11B 27/031 |

OTHER PUBLICATIONS

Saidov, Tamerlan, et al., "Contrast ultrasound dispersion imaging of different tumor types," 10.1109/ULTSYM.2012.0536, 2012 IEEE International Ultrasonics Symposium Proceedings, pp. 2149-2152.

Van Sloun, Ruud JG, et al., "Imaging of the Dispersion Coefficient of Ultrasound Contrast Agents by Wiener System Identification for Prostate Cancer Localization," 10.1109/ULTSYM.2015.0479, 2015 IEEE International Ultrsonics Symposium Proceedings, pp. 1-4.

Van Sloun, Ruud JG, et al., "Ultrasound-contrast-agent dispersion and velocity imaging for prostate cancer localization," Medical Image Analysis 35 (2017), pp 610-619.

Kuenen, M.P.J., "Contrast-ultrasound dispersion imaging for prostate cancer localization," Doctoral Thesis, Eindhoven: Technische Universiteit Eindhoven DOI: 10.6100/IR769554, XP055319527, 2014, 162 pages.

International Search Report and Written Opinion for PCT Patent App. No. PCT/EP2016/071191 (dated Nov. 29, 2016).

* cited by examiner

IMAGING OF DISPERSION AND VELOCITY OF CONTRAST AGENTS

CROSS REFERENCE TO RELATED APPLICATION(S)

This application is a National Phase Filing under 35 C.F.R. § 371 of and claims priority to PCT Patent Application No. PCT/EP2016/071191, filed on Sep. 8, 2016, which claims the priority benefit under 35 U.S.C. § 119 of European Patent Application Nos. 15184473.5 and 16171625.3, filed on Sep. 9, 2015, and May 27, 2016, respectively, the contents of each of which are hereby incorporated in their entireties by reference.

BACKGROUND

Some embodiments relate to a system and method of estimating a velocity of a contrast agent.

Cancer is a leading cause of death. Most solid tumors show angiogenic activity in order to receive nutrients and grow beyond few millimeters. Angiogenesis is the process leading to the formation of a dense network of micro vessels showing irregular architecture and structure. Angiogenic microvascularization is especially characterized by the presence of irregular branching and arteriovenous shunts, as well as by a higher degree of tortuosity and vascular permeability. Based on this, several imaging methods have been developed aiming at detecting the presence of angiogenic activity and microvascular network. However, these methods are based on the assessment of flow and perfusion, typically by Doppler of contrast-enhanced imaging. This measurement is complicated by the low values of blood flow in the micro vessels, requiring high sensitivity measurements, as well as by the controversial link between angiogenesis and perfusion. The limited spatial resolution of the available imaging techniques relative to the micro vessel size (10-micron diameter), is also a limiting factor. Recently, a new method has been introduced by contrast-enhanced MRI and ultrasound that permits the local estimation of a parameter related to the dispersion kinetics of a contrast agent flowing through a microvascular network. To this end, a solution of the convective diffusion equation is adopted and fitted to indicator dilution curves (IDCs) measured at each location after the intravenous injection of a contrast agent bolus. The dispersion kinetics of the agent reflects the microvascular architecture, being mainly determined by multipath trajectories. The results show the potential of the method. However, only the ratio between convection (squared velocity) and dispersion can be estimated, as well as some surrogates of dispersion based on similarity analysis.

Prostate cancer (PCa) is the most frequently diagnosed cancer in men aside from skin cancer, and the second-leading cause of cancer death in men. Given the significant risk of serious side effects associated with PCa treatment (radical prostatectomy), careful observation (termed active surveillance) instead of immediate treatment is appropriate for many patients that have less aggressive tumors. This approach requires accurate and reliable monitoring techniques. When treatment is necessary, minimally invasive methods such as focal therapy may limit side effects, which in turn requires accurate tumor localization. The current golden standard for prostate cancer diagnosis is transrectal systematic needle biopsies. However, initial biopsies miss nearly a quarter of the clinically significant cancers, and provide little information regarding exact tumor locations. Moreover, being an invasive technique, it carries significant risk of infection. This requires hospitalization in up to 6% of the cases, becoming even more alarming with increasing resistance to antibiotics.

Diffusion tensor MRI (DT-MRI) was the first non-invasive in-vivo imaging modality that enables the generation of fiber trajectories in soft fibrous tissues, such as nerves and muscles. It is based on the anisotropic nature of water diffusion in well-ordered structures, i.e. the water molecules have a preferred direction of diffusion in fibrous structure. After estimating its principle orientation in each image pixel, the streamlines of the resulting vector field are generated, visualizing the fiber tracts.

In Dynamic Contrast-Enhanced Ultrasound imaging (DCE-US), the passage of an intravenously injected bolus of ultrasound contrast agents (UCAs) through an organ of interest is recorded with an ultrasound imaging system. DCE-US is a minimally invasive diagnostic tool that allows analysis of vascularization, by imaging the intravenously injected microbubble bolus. Of particular interest is the localization of neo-angiogenic vasclularization associated with tumor growth and metastasis.

The microvascular structure that originates from tumor driven angiogenic growth is characterized by high microvascular density (MVD), small-diameter vessels that are highly tortuous, chaotic, irregular and have shunts. Ineffective blood flow can lead to hypoxia and deteriorated endothelial wall cells, potentially resulting in extra-vascular leakage and tumor metastases.

With the aim of detecting angiogenic microvascularization, DCE-US imaging of hemodynamic features relies on the hypothesis that these features reflect changes in microvasculature associated with angiogenesis. Focusing at increased MVD, time-intensity features related to microvasuclar perfusion have been studied by several researchers. However, ultrasound attenuation and scanner settings affect the estimation of local UCA concentration and the resulting amplitude based perfusion parameters. Moreover, increased tortuousity as well as increased flow resistance due to decreasing functional vascular cross-sectional area in neoplastic tissue cause lower tumor perfusion, leading to perfusion heterogeneity and making localization of angiogenesis based on perfusion a challenging task. Related to this, intra-tumor vascular heterogeneity has been assessed, although using DCE-CT instead of DCE-US. To enhance the sensitivity of perfusion imaging, regularized deconvolution of the perfused tissue signals with the feeding-artery signal (referred to as arterial input function) is investigated for DCE-CT and DCE-MRI in other research.

Alternatively, features linked to UCA bolus dispersion have been proposed, and are instead intended to directly reflect the tortuous and chaotic structure of the tumor vasculature. Although these approaches have shown promise, independent estimation of dispersion and velocity was not possible due to the ambiguity between dispersive and convective processes reflected in the measured IDCs. Hence, so far only dispersion related parameters that represent a combination of dispersion and velocity were obtained, leaving the specific contribution of both components to the flow kinetics unassessed. Furthermore, to achieve a local estimate of the contrast kinetics, a specific spatial UCA bolus concentration profile was assumed, see Kuenen et al, "Contrast-ultrasound diffusion imaging for localization of prostate cancer.", IEEE transactions on medical imaging, 2011.

SUMMARY

In summary, based on the current state of the related art, the following limitations are still present. Dispersion imaging is based on the analysis of single indicator dilution curves (IDC's) and does not allow for the estimation of contrast agent dispersion and velocity due to their ambiguity in single IDCs. Hence only parameters related to dispersion and velocity are identifiable, without solving them individually.

It may therefore be beneficial to provide an improved or enhanced method for achieving an estimate of the contrast agent velocity in vascular networks.

This goal is achieved by providing a method of estimating a velocity of a contrast agent, the method including:
  receiving a plurality of video frames that were produced using a dynamic contrast enhanced imaging process, each video frame including a plurality of pixels/voxels;
  defining a local kernel, the local kernel including a number of neighboring pixels/voxels;
  placing the local kernel at a first location relative to the video frames;
  determining indicator-dilution curves for the pixels/voxels in the local kernel using the received plurality of video frames;
  comparing the indicator-dilution curves between two of a pair of pixels/voxels for a number of pairs of pixels/voxels within the local kernel to obtain a spatiotemporal dependency of the concentration evolution between the pixels/voxels within the local kernel;
  repeating the step of comparing the indicator-dilution curves after having relocated the local kernel, until no relocation of the local kernel is needed;
  estimating the velocity for at least some of the pixels/voxels of the video frames using the spatiotemporal dependency;
  rendering the estimated velocity in a 2D or 3D image.

The velocity can be obtained using the spatiotemporal dependency by fusing information on the spatial location of the pixels/voxels at which the indicator-dilution-curves are measured and a temporal dependency between those indicator-dilution-curves. The temporal dependency can incorporate causality and measures of contrast agent transition time between pixels/voxels, e.g. time-delay, along with additional parameters that characterize the response of the path between those pixels/voxels, e.g. dispersion. Estimation of this temporal dependency, along with fusion of information on the spatial location of the pixels/voxels and the temporal dependency can be performed according to the embodiments described below.

In an embodiment, the step of estimating the velocity includes:
  determining a convection-diffusion model using the spatiotemporal dependency;
  identifying the convection-diffusion model to obtain the velocity and dispersion values.

So besides the velocity also the dispersion values are estimated independently from the velocity. These dispersion values may give an indication of the presence of angiogenesis.

In an embodiment, the method includes:
  determining an indicator-dilution curve for a pixel/voxel located at the center of the local kernel to obtain an input indicator-dilution curve;
  defining the indicator-dilution curves of the pixels/voxels of the local kernel as output indicator-dilution curves;
  defining Wiener-Hopf equations that describe the relation between the autocorrelation function of the input indicator-dilution curve and the cross-correlation function between the input indicator-dilution curve and output indicator-dilution curves;
  solving the Wiener-Hopf equations to obtain Wiener filter coefficients that represent a local channel impulse response, describing the spatiotemporal dependency;
  defining the convection-diffusion model in terms of the Wiener filter coefficients;
  solving the convection-diffusion model by model fitting the Wiener coefficients to obtain the velocity at at least some of the pixels/voxels.

In an embodiment, the method includes:
  converting the convection-diffusion model into a discrete Markov process, wherein a temporal prediction of the process states, being the contrast agent concentration over space, are defined in terms of current process states, a time step, and process model parameters being the velocity and the dispersion;
  augmenting the state vector with the velocity and dispersion;
  estimating the process state by filtering the indicator-dilution curves for all the pixels/voxels in the local kernel.

In an embodiment, the method includes:
  adding one or more compartments to the convection-diffusion model to be identified to obtain a compartment model;
  modeling extravasation kinetics of extravascular agents and the binding kinetics of targeted agents using the compartment model.

The extravasation kinetics and binding kinetics of targeted agents may give an indication of the presence of angiogenesis.

In an embodiment, the method includes:
  combining the estimated velocity and the dispersion values into a quantity by arithmetic operations or machine learning algorithms;
  generating the 2D or 3D image using the quantity.

The indications of the presence of angiogenesis that may be given by the dispersion and velocity values can be fused to obtain a map that may give an improved indication of the presence of angiogenic regions in tissue.

In an embodiment, the method includes:
  estimating the Péclet number for at least some of the pixels/voxels using the formula:

$$Pé=L*(v/D)$$

wherein Pé is the Péclet number, L is a characteristic length, v is the velocity and D is the dispersion value.

The Péclet number is a characteristic parameter that describes fluid-dynamic systems, and may be used to indicate the presence of angiogenesis since angiogenesis alters the fluid-dynamics in a vascular system.

In an embodiment, the method includes:
  estimating a plurality of time-delays ($\tau$) between the temporal evolutions of contrast agent concentration obtained within the pixels/voxels in the local kernel,
  determining the velocity by mapping the plurality of estimated time-delays to the spatial domain.

The contrast agent velocity including directionality provides information that can be used in other embodiments to assess angiogenesis, along with other aspects of flow.

In an embodiment, the mapping is obtained by solving a set of equations that describes a relation between time-delays, inter-pixel/voxel distance vectors and a velocity vector. The set of equations can be solved using weighted least squares minimization, where the weights may unity, i.e. all equal to 1, or a vector that gives measure of confidence for each estimated time-delay in the set of equations. The weights may be used to improve the reliability of the velocity estimates.

In an embodiment, the method includes:
impulse response identification amongst a set of indicator dilution curves within the local kernel to obtain time parameters and a mean transit time value (μ).

The impulse response identification may be performed using a parametric model such as:
Local Density Random Walk model;
Lognormal model;
Gamma-variate model;
Erlang function, or
Lagged Normal function.

It is noted that time-delays are affected by contrast agent velocity, but also by other components of contrast agent flux, including dispersion/diffusion. Impulse response identification enables assessing all components independently.

In an embodiment, the method further includes characterization of a velocity vector field, wherein the characterization is performed using one of the following methods:
statistical characterization by calculating the velocity field's entropy;
pattern recognition with machine learning.

Angiogenic vasculature is characterized by irregular architectures that may be reflected in the velocity vector field. Characterization of the velocity vector field may therefore indicate the presence of angiogenesis.

In an embodiment, the method further includes:
generating a 2D or 3D representation of ultrasound-contrast-agent trajectories, the representation including a most likely vascular structure, via a predetermined number of seed particles that are associated with a path within the estimated 2 or 3-dimensional velocity vector field.

The generating a 2D or 3D representation may include:
initializing a predetermined set of particles at seed points;
tracking the ultrasound-contrast-agent trajectories at the seed point;
determining, for each particle, a propagation direction based on the velocity vectors and moving each particle by a predetermined step size in the projection direction.

In this way trajectories may be determined that represent what are most likely vascular structures. Alterations in the vascular structure due to angiogenesis may be revealed by these trajectories.

In an embodiment, the method further includes an assessment of vascular features based on the representation of ultrasound-contrast-agent trajectories, wherein the vascular features include representations of at least one of Tortuosity, Density, Branching, Fractality and Regularity. All of these measures may provide evidence for angiogenesis.

According to a further aspect, there is provided an estimating system for estimating a velocity of a contrast agent, the system including:
an input module for receiving a plurality of video frames that were produced using a dynamic contrast enhanced imaging process, each video frame including a plurality of pixels/voxels;
an image processing module for:
defining a local kernel, the local kernel including a number of neighboring pixels/voxels;
placing the local kernel at a first location relative to the video frames;
determining indicator-dilution curves for the pixels/voxels in the local kernel using the received plurality of video frames;
comparing the indicator-dilution curves between two of a pair of pixels/voxels for a number of pairs of pixels/voxels within the local kernel to obtain a spatiotemporal dependency of the concentration evolution between the pixels/voxels within the local kernel;
repeating the step of comparing the indicator-dilution curves after having relocated the local kernel, until no relocation of the local kernel is needed;
an estimating module for estimating the velocity for at least some of the pixels/voxels of the video frames using the spatiotemporal dependency;
an output module for rendering the estimated velocity in a 2D or 3D image.

The system may include a solving module for solving a convection-diffusion model using the plurality of video frames to obtain a measure of the spatiotemporal evolution of the contrast agent concentration.

The system may further include:
an estimator configured for estimating a plurality of time-delays (τ) between the temporal evolutions of contrast agent concentration obtained within the pixels/voxels in the local kernel, and
a velocity determinator configured for determining the velocity by mapping the plurality of estimated time-delays to the spatial domain.

The system may further include an identification module configured for impulse response identification amongst a set of indicator dilution curves within the local kernel to obtain time parameters and a mean transit time value (μ).

The system may further include a module configured for determination of ultrasound-contrast-agent trajectories based on the velocity.

BRIEF DESCRIPTION OF THE DRAWINGS

These and other aspects of some embodiments are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

In an embodiment, a velocity of a contrast agent is estimated by first receiving a plurality of video frames that were produced using a dynamic contrast enhanced imaging process. Each video frame includes a plurality of pixels or voxels (2D or 3D images) further referred to as pixels/voxels. A so-called local kernel is defined including a number of neighboring pixels/voxels. The local kernel is placed at a first location relative to the video frames and next indicator-dilution curves are determined for the pixels/voxels in the local kernel. The indicator-dilution curves are compared between two of a pair of pixels/voxels for a number of pairs of pixels/voxels within the local kernel to obtain a spatiotemporal dependency of the concentration evolution between the pixels/voxels within the local kernel.

Figure 1A:
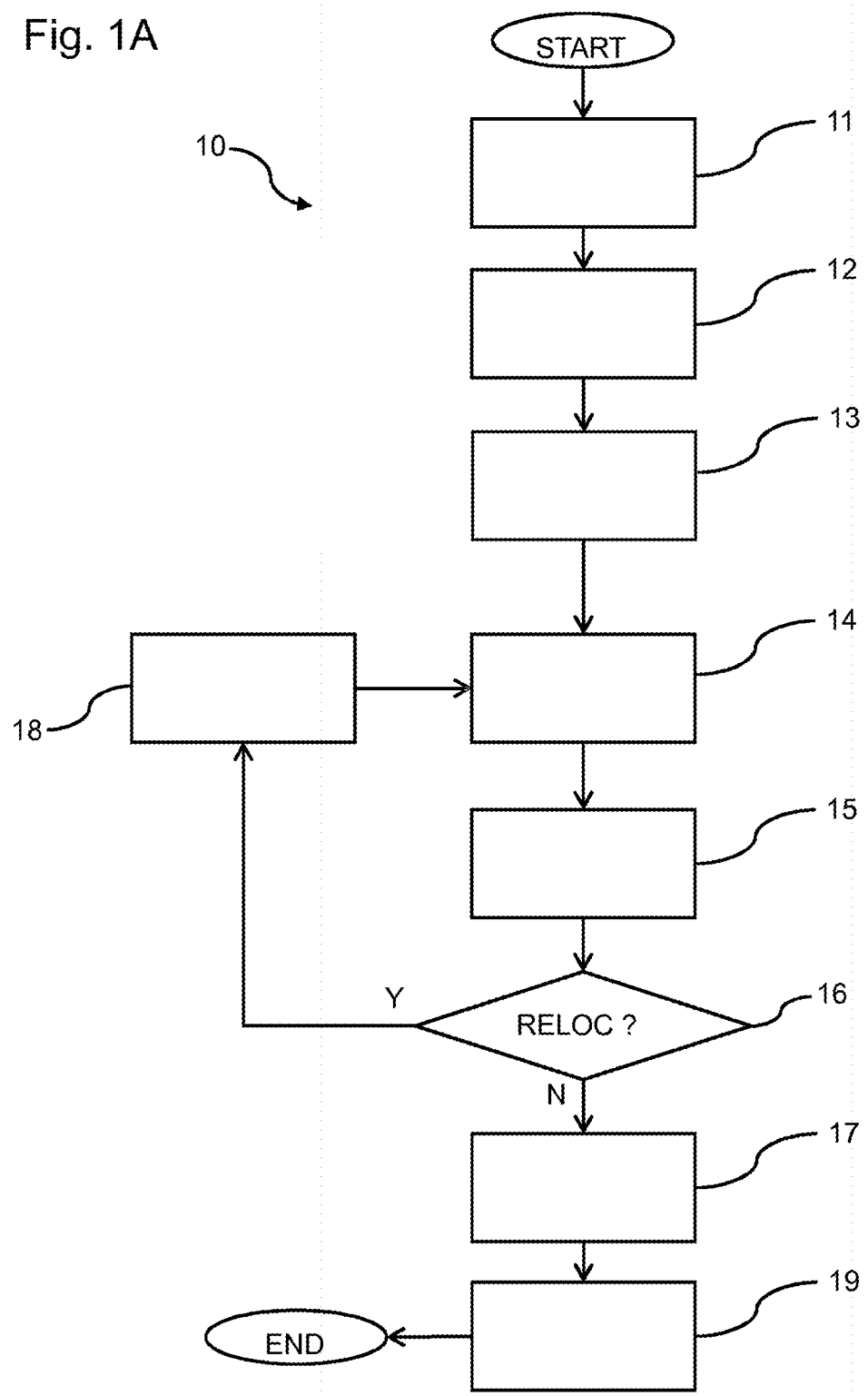
FIG. 1A shows a flow chart of the method of estimating a velocity of a contrast agent according to an embodiment.

FIG. 1A shows a flow chart of the method 10 of estimating a velocity of a contrast agent according to an embodiment. In FIG. 1A a block 11 represents the receiving a plurality of video frames that were produced using a dynamic contrast enhanced imaging process, each video frame including a plurality of pixels/voxels. A block 12 represents the defining a local kernel, the local kernel including a number of neighboring pixels/voxels. A block 13 represents the placing the local kernel at a first location relative to the video frames. A block 14 represents the determining indicator-dilution curves for the pixels/voxels in the local kernel using the received plurality of video frames. A block 15 represents the comparing the indicator-dilution curves between two of a pair of pixels/voxels for a number of pairs of pixels/voxels within the local kernel to obtain a spatiotemporal dependency of the concentration evolution between the pixels/voxels within the local kernel.

A block 16 represents a test whether a relocation of the local kernel is needed. If there is no need for a relocation, the method continues with a block 17 which represents the estimating the velocity for at least some of the pixels/voxels of the video frames using the spatiotemporal dependency, otherwise the method goes to a block 18 which represents relocating the local kernel and block 14 is performed again.

Finally at a block 19 the rendering the estimated velocity in a 2D or 3D image is executed.

Figure 1B:
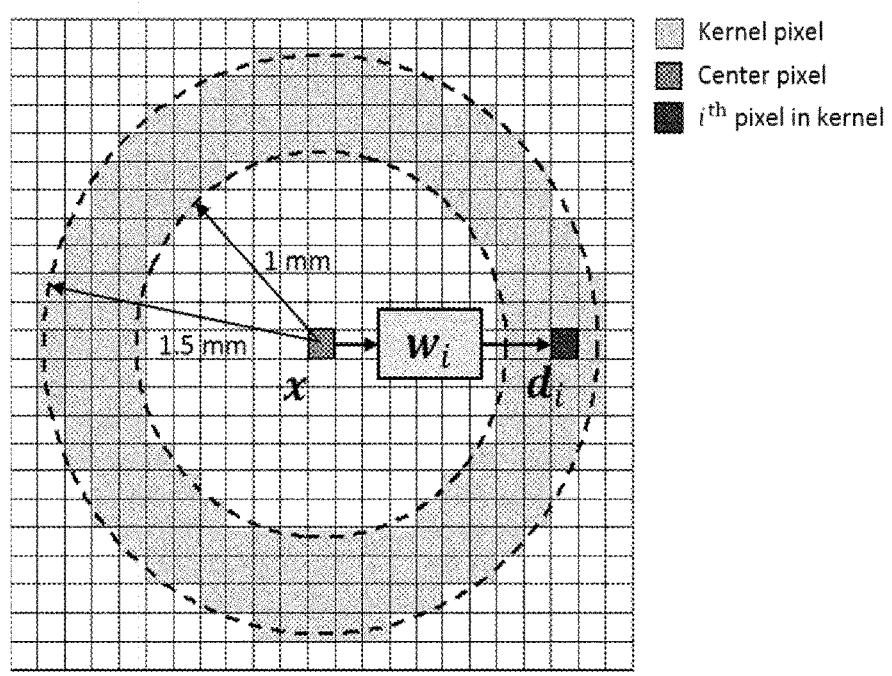
FIG. 1B schematically shows a representation of a ring kernel used for impulse response estimation according to an embodiment.

FIG. 1B schematically shows a representation of the local kernel, in this example being a ring kernel used for impulse response estimation according to an embodiment. The ring kernel includes a center pixel x and a number of surrounding pixels d, located inside a ring around the center pixel x. In this example an inner and outer radius of the kernel are 1~mm and 1.5~mm respectively.

To estimate the local ultrasound Contrast Agent (UCA) bolus dynamics, channel impulse responses are determined using the ring kernel and a model. In this model, it is assumed that the IDC of a pixel $d_i$ within the ring (output) is a filtered version of the IDC of the pixel at the center (input). Wiener filter coefficients $w_i$ that represent the local channel can then be found by solving the Wiener-Hopf equations, describing the relation between the input autocorrelation and input-output cross-correlation. A reference is provided in relation to the Wiener-Hopf equation and the reference is incorporated by reference: Papoulis A. Probability, "Random Variables, and Stochastic Processes." McGraw-Hill Companies; 1991.

A differential model that represents the hemodynamics captured in the Wiener filter coefficients $w_i$ can be described by a one-dimensional convection-diffusion equation. The model parameters, being dispersion and velocity, can then be obtained by e.g. a Maximum Likelihood parameter estimation or using any other model-fitting approach. See for example, Kuenen M P, et al, "Maximum-likelihood estimation for indicator dilution analysis", IEEE Transactions on Biomedical Engineering 2014; 61:821-831. Or see for example, Bishop C M. "Pattern Recognition and Machine Learning.", Springer; 2006. Kuenen et al and Bishop. Both articles are incorporated by reference.

Figure 2:
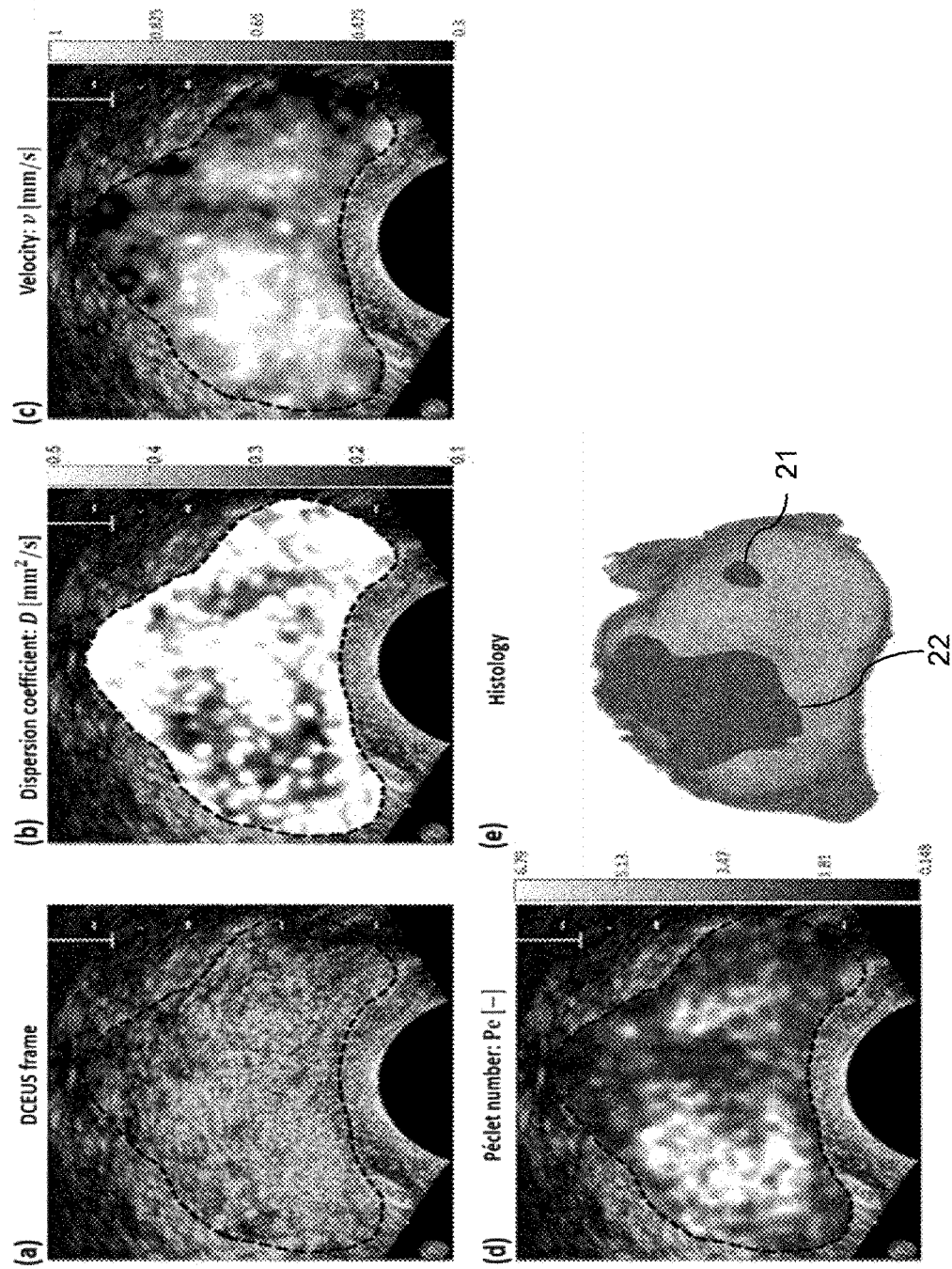
FIG. 2A-2E show an example of a DCE-US frame together with the hemodynamic parametric images and a histology slice.

An example of the above described embodiment applied to 2D DCE-US imaging data is given in FIG. 2. FIG. 2 shows an example of a DCE-US frame (FIG. 2a), together with the hemodynamic parametric images showing (FIG. 2b) the local dispersion coefficient, (FIG. 2c) the local velocity and (FIG. 2d) the Péclet number. The corresponding histology slice is shown in (FIG. 2e), with marked malignant areas, see areas 21, 22. As can be seen from FIGS. 2b-2d, the estimated parameters indicate the presence of malignant areas as determined from histology.

According to an embodiment, a spatiotemporal evolution of the contrast agent kinetics is modeled as a convection-dispersion process, and represented as a discrete Markov process. A temporal prediction of the system states, being the contrast agent concentration over space, can be defined in terms of the current system states, the time step, and the model parameters (multidimensional velocity and dispersion).

The discretized process described in Siegel R, Ma J, Zou Z, Jemal A. Cancer statistics, 2014. CA Cancer J Clin 2014; 64:9-29, which is incorporated by reference, can be captured with the possibly nonlinear observation (imaging data) in a state space model with a process covariance matrix and process noise, as well as observation noise. The (non-)linear observation model describes contrast agent concentration to image quantization level mapping.

Optimal filtering, possibly in the form of but not limited to a Kalman filter, Extended Kalman filter, Ensemble Kalman Filter or Particle filter, can be used for process state estimation. More information about such filtering can be found in, which is incorporated by reference, Simon D. "Optimal State Estimation: Kalman, H Infinity, and Nonlinear Approaches.", Wiley, 2006.

Joint state and parameter estimation can be performed by augmenting the state vector with the process model parameters.

Figure 3:
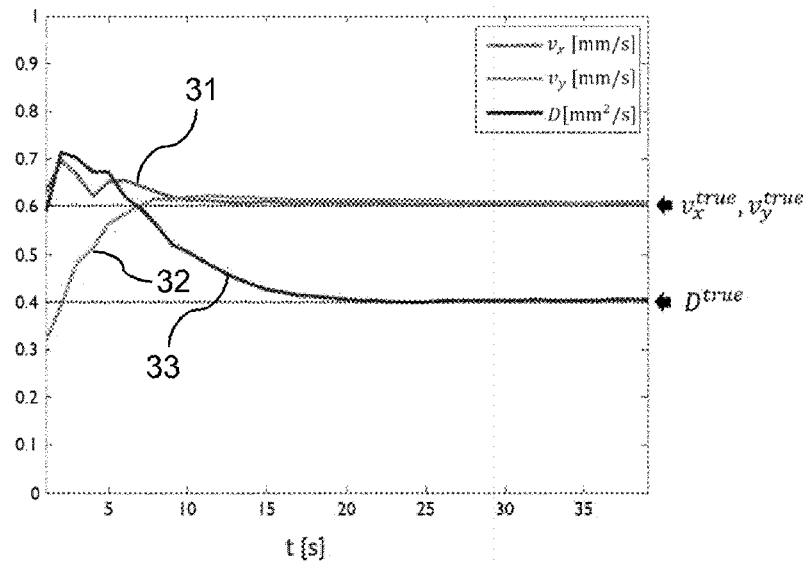
FIG. 3 shows a graph of a 2D velocity vector and isotropic dispersion estimation using spatiotemporal identification of the underlying process from simulated measurement data.

FIG. 3 shows a graph of a 2D velocity vector and isotropic dispersion estimation using spatiotemporal identification of the underlying process from simulated measurement data. In FIG. 3 a line 31 indicates the $v_x$ as a function of time, a line 32 indicates $v_y$ as a function of time and a line 33 indicates the dispersion D as a function of time. As can be seen from FIG. 3, all three model parameters converge to a specific value which gives the true model parameters. Here, the true model parameters are the model parameters used in the data simulation.

Figure 4:
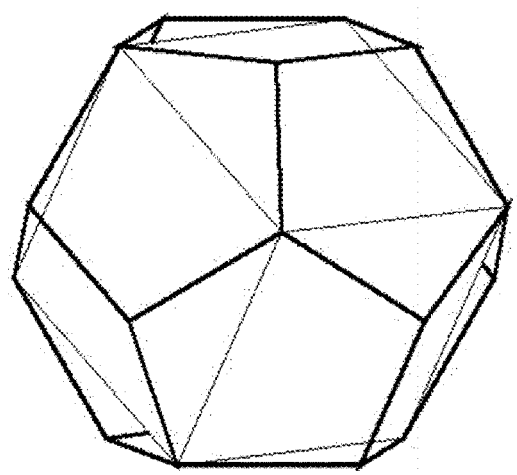
FIG. 4 shows an example of a 3D kernel.

Now some further details of the embodiments will be discussed. In the discussion below 2D video frames (i.e. 2D images) are assumed wherein a 2D local kernel is used. It is noted that in case of 3D image data a 3D kernel should be used, an example of which is shown in FIG. 4. FIG. 4 shows a dodecahedron with equal distances between the nodes that determine the voxels that should be selected for the analysis. Other 3D kernels can for instance include the set voxels that are the closest to a distribution of nodes on a sphere, or even all voxels within a sphere. A sphere (or circle in 2D) is convenient since it preserves angular symmetry, but possible kernels are not limited to this shape.

As was shown in FIG. 1B, a ring shaped kernel is used in an embodiment with an inner and outer radius of 1 mm and 1.5 mm, respectively. These dimensions are based on the speckle-grain size and the scale at which early angiogenesis occurs, i.e. preferably larger than the system resolution and smaller than the scale at which angiogenesis has to be detected. The adopted kernel is used as follows. The IDC of the center-pixel is considered to be the local channel input, and the IDCs of the surrounding pixels in the kernel are the possible outputs of the channel. Firstly, the channel impulse responses from the input to the outputs are estimated. Then, all non-causal responses are discarded, after which a mean causal impulse response is obtained.

To accomplish this, the IDC of the $i^{th}$ pixel within the kernel $d_i \in \mathbb{R}^N$ is modelled as a filtered version of the IDC of the pixel at the center $x \in \mathbb{R}^N$. Minimizing the mean squared error between the desired output $d_i[n]$ and the filtered input $\Sigma_{m=0}^{n-1} w_i[m] \times [n-m]$, the optimal Wiener filter coefficients $w_i$ are given by the Wiener-Hopf equations:

$$r_{d_i x} = R_x w_i, \quad (1)$$

where $r_{d_i x}$ denotes the cross correlation vector between $d_i$ and x and $R_x$ is the autocorrelation matrix of x. In practice, ultrasonic IDC measurements are corrupted by multiplicative (e.g. speckle) as well as additive (e.g. thermal, electronic) noise. Their effects are first analyzed on the Wiener estimate, and consider noisy observations $$\tilde{x} = u_1 x + v_1,$$

$$\tilde{d}_i = u_2 d_i + v_2,$$

with $v_1$, $v_2$ being independent and identically distributed (i.i.d.) white $\mathcal{N}(0, \sigma_v^2)$ and $u_1$, $u_2$ following i.i.d. Rayleigh distributions with scale parameter $\sigma_u$, being mutually independent and independent of the signal components. The local assumption on equal noise variances of $u_1$ and $u_2$ is reasonable given the small kernel size. A Rayleigh distribution was chosen because it captures the effects of fully developed speckle noise in ultrasound. The measured cross correlation vector is then given by $$r_{\tilde{d}_i \tilde{x}} = E[u_1] E[u_2] r_{d_i x} = \frac{\pi}{2} \sigma_u^2 r_{d_i x}, \quad (4)$$

where $E[\cdot]$ denotes the expectation. Similarly, the measured autocorrelation matrix of 2 can be derived as $$R_{\tilde{x}} = R_{u_1} R_x + \sigma_v^2 I, (2) \quad (5)$$

where $R_{u_1}$ is the autocorrelation matrix of the multiplicative noise component and I denotes the identity matrix. Assuming a white Rayleigh distribution, the following autocorrelation function is available:

$$r_{u_1}(\tau) = \delta(\tau) \int_0^\infty u^2 \frac{u}{\sigma_u^2} \exp\left(-\frac{u^2}{2\sigma_u^2}\right) du = 2\sigma_u^2 \delta(\tau),$$

where $\delta(\tau)$ is the Dirac delta function, for which $$R_{u_1} = 2\sigma_u^2 I.$$

Subsequently, the true signal autocorrelation matrix and cross correlation vector may be estimated from the measured data. The latter can directly be estimated from formula (4) as:

$$\hat{r}_{d_i x} = \frac{2}{\pi} \frac{r_{\tilde{d}_i \tilde{x}}}{\sigma_u^2}. \quad (8)$$

Estimating the autocorrelation matrix $R_x$ is less trivial. With the aim of separating the signal and noise subspaces, first an eigende composition is performed on (5), yielding $$R_{\tilde{x}} = [U_x \ U_v] \begin{bmatrix} 2\sigma_u^2 \Lambda_x + \sigma_v^2 & 0 \\ 0 & \sigma_v^2 \end{bmatrix} \begin{bmatrix} U_x^H \\ U_v^H \end{bmatrix}, \quad (9)$$

where $\Lambda_x$ is a diagonal matrix whose elements are the corresponding signal eigenvalues, i.e. $\Lambda_x(n,n) = \lambda_x(n)$, arranged in descending order. $U_x$ and $U_v$ denote the signal and noise subspaces, respectively. From formula (9), the signal subspace can readily be obtained by simply observing the eigenvalues $\lambda_{\tilde{x}}(n)$. However, this approach assumes $R_{\tilde{x}}$ to be estimated from an infinite sample size. In practice, the number of observations is limited, and R, is estimated by the sample-autocorrelation matrix, with noise eigenvalues that are all different. Hence formula (9) does not hold, and estimation of the signal subspace becomes more challenging.

Figure 5:
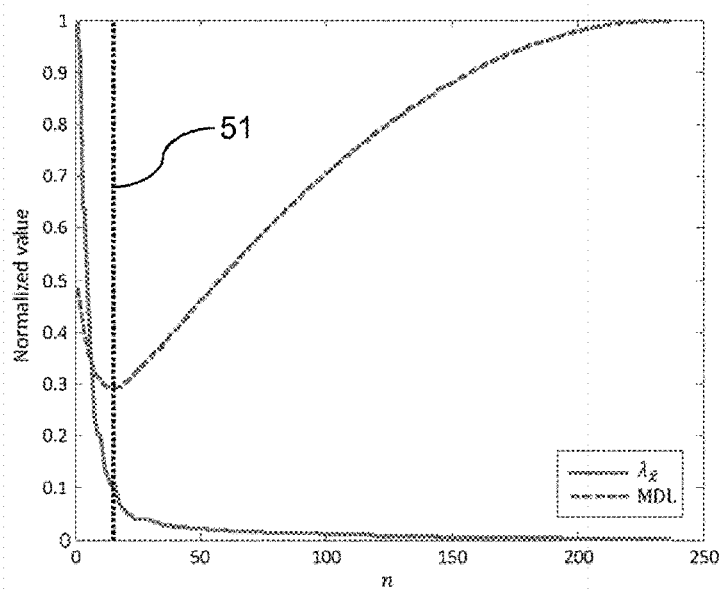
FIG. 5 shows a graph of Eigenvalues $\lambda_{\tilde{x}}$ as well as the Minimum Description Length (MDL) criterion for an example sample-autocorrelation matrix.

FIG. 5 shows a graph of Eigenvalues $\lambda \tilde{x}$ as well as the Minimum Description Length (MDL) criterion for an example sample-autocorrelation matrix. The value of n that minimizes the MDL is indicated by the dashed vertical line 51, here being n=16.

To overcome the problem of subspace selection given limited observation, the subspace detection is regarded to be a model selection problem. Given the observations that are used to acquire the sample-autocorrelation matrix, along with a set of models parameterized by n signal eigenvalues and n eigenvectors in addition to a noise variance, the model that best fits the observations is selected. A reference is made to Wax, Mati, et al, 1985, "Detection of Signals by Information Theoretic Criteria.", *IEEE Transactions on Acoustics, Speech and Signal Processing* 33 (2), IEEE: 387-92, and the article is incorporated by reference. Adopting the approach developed by Wax, Mati, et al, 1985, the Minimum Description Length (MDL) describes a trade-off between the log-likelihood of the maximum likelihood estimator of the model parameters (i.e. the sample eigenvalues and eigenvectors) and a term promoting a low number of free parameters:

$$MDL(n) = -\log\left[\frac{\prod_{l=n+1}^{N}(\lambda_{\tilde{x}}(l))^{\frac{1}{N-n}}}{\frac{1}{N-n}\sum_{l=n+1}^{N}\lambda_{\tilde{x}}(l)}\right]^{(N-n)M} + \frac{1}{2}n(2N-n)\log M,$$

where $\lambda\tilde{x}(l)$ is the $l^{th}$ eigenvalue of the sample-autocorrelation matrix $R_{\tilde{x}}$ and M is the number of samples used to compute $R_{\tilde{x}}$. The dimension of the signal subspace $\hat{n}$ is then determined as the value of n that minimizes the MDL. This procedure is exemplified in FIG. 2. From this, an estimate of $R_x$ can be obtained as:

$$\hat{R}_x = \frac{1}{2\sigma_u^2}\hat{U}_x[\hat{\Lambda}_x - \sigma_v^2]\hat{U}_x^H,$$

where $\hat{\Lambda}_x$ and $\hat{U}_x$ are the estimated signal eigenvalues and eigenvectors, respectively. To enable computation of the Wiener coefficients $w_i$, an estimate of $R_x^{-1}$ is also given. Since matrix inversion can be instable and prone to noise amplification, a strategy is employed based on eigenvalue regularization. Given the measured eigenvalues $\lambda_{\tilde{x}}(n)$, the regularized eigenvalues are given by:

$$\hat{\lambda}_x(n) = \begin{cases} \lambda_{\tilde{x}}(n) & \text{if } n \leq \hat{n} \\ \lambda_{\tilde{x}}(\hat{n}+1) & \text{otherwise} \end{cases}, \quad (12)$$

after which inversion of the autocorrelation matrix is achieved by inverting the regularized eigenvalues:

$$\hat{R}_x^{-1} = 2\sigma_u^2 U_{\tilde{x}} \begin{bmatrix} 1/\hat{\lambda}_x(1) & 0 & 0 \\ 0 & \ddots & 0 \\ 0 & 0 & 1/\hat{\lambda}_x(N) \end{bmatrix} U_{\tilde{x}}^H. \quad (13)$$

Next, an estimate is obtained of the Wiener filter coefficients $$\hat{w}_i = \hat{R}_x^{-1}\hat{r}_{d_ix},$$

describing the channel from x to $d_i$. Note that the noise variance $\sigma_u^2$ cancels out. Using this, the mean causal impulse response $\bar{w}$ is calculated by averaging the obtained coefficients over all kernel IDC's $d_i$ that show a causal relation with respect to the center IDC x:

$$\bar{w} = \frac{1}{|S_c|}\sum i \in S_c \hat{w}_i,$$

where $S_c$ denotes the set of causal impulse responses, and $|S_c|$ is the number of causal impulse responses. Causality between an IDC in the kernel ring and the IDC at the center pixel is assumed if the peak time of the cross correlation vector $\hat{r}_{d_ix}$ is positive.

To provide a parameter-based characterization of the estimated mean Wiener channel, a macroscopic view of the vascular network may be taken by regarding the flow through all the multi-path trajectories similar to the flow through porous media. In line with this, the differential model that has been adopted to represent the hemodynamics captured in $\bar{w}$, is the one-dimensional convection-diffusion equation with constant diffusion and velocity within the kernel:

$$\partial_t C(z,t) = D\partial_z^2 C(z,t) - v\partial_z C(z,t), \quad (16)$$

where $C(z,t)$ is the contrast agents concentration at position z and time t, D is the diffusion coefficient, describing the apparent dispersion of contrast agents through the vascular network and v is the convective velocity.

Being closer to the observed macroscopic physical phenomena of UCAs flowing through multi-path vascular trajectories, to D will be referred as the dispersion coefficient rather than the molecular diffusion. From (16), a goal is the estimation of v and D. To this end, its Green's function can be derived as, $$g(z,t\,|\,v,D) = \frac{H(t)}{\sqrt{4\pi Dt}}\exp\left(-\frac{(z-vt)^2}{4Dt}\right), \quad (17)$$

where $H(t)$ is the Heaviside step function, and can be curve-fitted to $\bar{w}$ using Least Squares (LS) minimization.

The position z is approximated by the average radial distance L=1.25 mm of pixels in the ring shaped kernel with respect to the center pixel. Obeying the conservation of mass, $g(L,t\,|\,v,D)/v$ has a temporal integral equal to one. However, if certain assumptions on the noise model or the estimation of its power are not entirely correct (e.g. unequal noise variances of $u_1$ and $u_2$), the amplitude of the Wiener estimate depends on the noise variances. Therefore, in an embodiment, a factor $\alpha$ is introduced, allowing the model to compensate for these mismatches. The resulting optimization problem can then be written as:

$$\{\hat{D}_{LS}(x), \hat{v}_{LS}(x)\} = \min_{D,v}\|\alpha g(v,D) - \bar{w}\|_2^2,$$

$$= \min_{D,v}\left\|\alpha g(v,D) - \frac{1}{|S_c|}\sum i \in S_c \hat{R}_x^{-1}\hat{r}_{d_ix}\right\|_2^2,$$

where $g(v,D) = [g[1|v,D] \ldots g[N|v,D]]$ is the discrete version of g(L, t|v, D). The challenging inversion of $\hat{R}_r$ can be addressed by regularization as given in (12) and (13). As the only interest is in the convection-diffusion model parameters, the inversion of the autocorrelation matrix can be avoided by rewriting the LS problem to:

$$\{\hat{D}_{LS}(x), \hat{v}_{LS}(x)\} = \min_{D,v}\left\|\alpha \hat{R}_x g(v,D) - \frac{1}{|S_c|}\sum i \in S_c \hat{r}_{d_ix}\right\|_2^2.$$

The Péclet number, being the well-known dimensionless number describing the ratio between the dispersive time and the convective time is then estimated as:

$$\hat{P}e_{LS} = L\frac{\hat{v}_{LS}}{\hat{D}_{LS}}.$$

So far it has been assumed the local dynamic transport of microbubbles to be a solely deterministic process. However, for low microbubble concentrations it may be more realistic to express it as a stochastic process. In fact, the probability that a number of microbubbles X is delayed by n time samples from x to $d_t$, may be modeled as a binomial distribution with an expected value determined by the local hemodynamics. Here, the probability mass function of individual particle transit times is assumed to be $p[n|v,D]=g[n|v,D]/|g(v,D)|_1$, where $|\cdot|_1$ denotes the $l_1$ norm. If the total number of particles K is high enough and the sample time is small enough, $p[n|v,D]$ can be approximated by a Poisson distribution, having a variance equal to the expected value:

$$P(X=k|\lambda) = \frac{\lambda^k e^{-\lambda}}{k!},$$

where $\lambda=E[X]=Var[X]=Kp[n|v,D]$. For the purpose of estimating the transport kinetics, this non-additive, signal-dependent variance is regarded as noise. Since the noise model is not following a normal distribution and is signal dependent, the Least Square (LS) solution does not yield minimum-variance estimation. In this case, a more suitable approach may be to use a Maximum Likelihood (ML) estimator, which is an asymptotically minimum-variance unbiased estimator that does not assume a specific noise distribution. The log likelihood of the model parameters $\theta=\{v,D\}$ is given by:

$$l(\theta) = \ln\prod_{n=1}^{N} P(X=k[n]|\lambda),$$

$$= \sum_{n=1}^{N} \ln\left(\frac{\lambda^{k[n]} e^{-\lambda}}{k[n]!}\right),$$

$$= \sum_{n=1}^{N} k[n]\ln(\lambda) - \lambda - \ln(k[n]!),$$

$$= \sum_{n=1}^{N} k[n]\ln\left(K\frac{g[n|\theta]}{|g(\theta)|_1}\right) - \frac{K}{|g(\theta)|_1}\sum_{n=1}^{N} g[n|\theta] - \sum_{n=1}^{N} \ln[k[n]!],$$

$$= \sum_{n=1}^{N} k[n]\ln\left(K\frac{g[n|\theta]}{|g(\theta)|_1}\right) - \sum_{n=1}^{N} \ln[k[n]!],$$

which can be maximized to obtain the model parameters $\theta$ as $$\hat{\theta} = \max_{\theta} \sum_{n=1}^{N} k[n]\ln\left(\frac{g[n|\theta]}{|g(\theta)|_1}\right).$$

Using that the number of particles that are delayed by n samples, k[n], is proportional to the corresponding estimated Wiener coefficient $\overline{w}[n]$, the following is obtained:

$$\hat{\theta} = \max_{\theta} \sum_{n=1}^{N} \overline{w}[n]\ln\left(\frac{g[n|\theta]}{|g(\theta)|_1}\right) \quad (24)$$

$$\approx \max_{\theta} \sum_{n=1}^{N} \overline{w}[n]\{\ln(g[n|\theta]) + \ln(v)\},$$

where use is made of the area under the curve $|g(\theta)|_1 \propto 1/v$ according to the Stewart-Hamilton equation.

Besides its advantages regarding the noise distribution, this specific ML problem has an analytical solution, which greatly reduces computational complexity with respect to the iterative approach required for the nonlinear LS problem. By taking the derivatives of (24) with respect to the model parameters and determining their zero crossings (see at "derivation of maximum likelihood estimation"), the following ML estimators for the velocity can be obtained:

$$\hat{v}_{ML} = L\frac{\sum_{n=1}^{N} \frac{\overline{w}[n]}{n\Delta t}}{\sum_{n=1}^{N} \overline{w}[n]},$$

where $\Delta t$ is the sample time, and the dispersion coefficient $$\hat{D}_{ML} = \frac{\sum_{n=1}^{N} \frac{\overline{w}[n]}{n\Delta t}[L-v(n\Delta t)]^2}{2\sum_{n=1}^{N} \overline{w}[n]}$$

$$= L^2 \frac{\sum_{n=1}^{N} \frac{\overline{w}[n]}{n\Delta t}\left(1 - \frac{\sum_{m=1}^{N} \frac{\overline{w}[m]}{m\Delta t}}{\sum_{m=1}^{N} \overline{w}[m]} n\Delta t\right)^2}{2\sum_{n=1}^{N} \overline{w}[n]}.$$

The Péclet number is then estimated as:

$$\hat{P}e_{ML} = L\frac{\hat{v}_{ML}}{\hat{D}_{ML}}.$$

Note that the ML approach requires the inversion of $\hat{R}_x$ to obtain $\overline{w}$.

Now the Maximum Likelihood estimators can be derived. Starting from the result of formula (24)

$$\hat{\theta} = \max_{\theta}\{l(\theta)\} \approx \max_{\theta} \sum_{n=1}^{N} \overline{w}[n]\{\ln(g[n|\theta]) + \ln(v)\},$$

the partial derivatives with respect to the model parameters v and D is taken, and is equated to zero:

$$\partial_v l(\theta) = \sum_{n=1}^{N} \overline{w}[n]\left\{\frac{\partial_v g(n|v,D)}{g(n|v,D)} + \frac{1}{v}\right\} = 0,$$

-continued $$\partial_D l(\theta) = \sum_{n=1}^{N} \overline{w}[n] \left\{ \frac{\partial_D g(n \mid v, D)}{g(n \mid v, D)} \right\} = 0,$$

which, when using (17) with sample time $\Delta T$, leads to $$\partial_v l(\theta) = \sum_{n=1}^{N} \overline{w}[n] \left\{ \frac{(L - vn\Delta t)}{2D} + \frac{1}{v} \right\} = 0, \quad (30a)$$

$$\partial_D l(\theta) = \sum_{n=1}^{N} \overline{w}[n] \left\{ \frac{(L - vn\Delta t)^2 - 2Dn\Delta t}{4D^2 n\Delta t} \right\} = 0. \quad (30b)$$

Next, after rewriting (30) the result is:

$$D \sum_{n=1}^{N} \overline{w}[n] = -\sum_{n=1}^{N} \overline{w}[n] \frac{v(L - vn\Delta t)}{2}, \quad (31a)$$

$$D \sum_{n=1}^{N} \overline{w}[n] = \sum_{n=1}^{N} \overline{w}[n] \frac{(L - vn\Delta t)^2}{2n\Delta t} = 0. \quad (31b)$$

Then, we subtract (31b) from (31a) to obtain:

$$\sum_{n=1}^{N} \overline{w}[n] \left\{ \frac{vL}{2} - \frac{L^2}{2n\Delta t} \right\} = 0,$$

from which the ML estimate of the velocity can be obtained as:

$$\hat{v}_{ML} = L \frac{\sum_{n=1}^{N} \frac{\overline{w}[n]}{n\Delta t}}{\sum_{n=1}^{N} \overline{w}[n]}.$$

Next, $\hat{v}_{ML}$ is used to solve (30b), and the ML estimate of the dispersion coefficient is obtained as:

$$\hat{D}_{ML} = \frac{\sum_{n=1}^{N} \frac{\overline{w}[n]}{n\Delta t} [L - v(n\Delta t)]^2}{2 \sum_{n=1}^{N} \overline{w}[n]}.$$

To validate the above described models, in vivo DCE-US investigations were performed. In total, 25 patients with biopsy-proven prostate cancer scheduled for radical prostatectomy were included in this study. The passage of a microbubble bolus through the prostate was obtained using an intravenous injection of 2.4-mL SonoVue (Bracco, Milan, Italy), and consecutively imaged using a 2D transrectal ultrasound probe (C10-3v) and a Philips iU22 ultrasound system (Philips Heathcare, Bothell, Wash.). To record the full in- and outflow, DCE-US acquisitions were performed during 120 s.

When insonified, microbubbles exhibit a resonating behavior that is strongly nonlinear with respect to the incident pressure. Exploiting this, a contrast agent-specific imaging mode based on a power modulation pulse scheme at 3.5 MHz was used to enhance sensitivity to microbubbles while suppressing linear backscattering from tissue. The mechanical index was set to 0.06, high enough to obtain sufficient echo signal power, however minimizing microbubble destruction.

Using the methods described in Kuenen et al., 2011, IEEE transactions on medical imaging, the relation between SonoVue concentration and acoustic intensity, along with the ultrasound scanner's compression function were determined and used to estimate the linearized IDCs from the measured acoustic intensity.

To evaluate the potential of the developed imaging method at localizing prostate cancer, a clinical validation was carried out using a dataset consisting of 63 DCE-US imaging planes recorded from 25 patients that underwent radical prostatectomy. Multiple planes ranging from base to apex where recorded per patient. After radical prostatectomy, histopathological analysis of the prostate was performed. The prostate was dissected in slices of 4-mm thickness, and a pathologist marked the presence of cancer according to what has been described by Montironi et al. 2003. Reference is made to the articles, which is incorporated by reference, Montironi, Rodolfo, et al, 2003, "Handling and Pathology Reporting of Radical Prostatectomy Specimens." *European Urology* 44 (6), Elsevier: 626-36. Based on the histology results, regions of interest (ROI) of approximately 0.5 cm$^2$ covering benign and malignant pixels were selected from the ultrasound data. To mitigate errors due to plane mismatch between ultrasound and histology, the ROI's were selected by considering tumors that occur throughout 3 neighboring histology slices. In total, the ROI's contained approximately 177×10$^3$ time intensity curves, of which 51% was taken from benign regions. After post-filtering the feature maps using a Gaussian spatial filter with a standard deviation $\sigma_{post}$=1.3 mm, pixel-based classification was performed. For each feature, the Receiver-Operating-Characteristics (ROC) curves were calculated, after which the optimal threshold was determined as a trade-off between sensitivity and specificity by selecting the point on the ROC curve that is closest to the ideal classification, i.e. the top-left corner. Based on this, the area under the ROC curve, sensitivity, specificity, positive predictive value (PPV), and negative predictive value (NPV) of the individual parameters were calculated.

The performance of the ML and LS estimators across the observations were compared by calculating p-values of the difference between their area under the ROC curve. The required standard errors related to the ROC area are computed according to Hanley and McNeil 1982, and are dependent on de number of independent samples. Reference is made to the article, which is incorporated by reference, Hanley, James A, and Barbara J McNeil, 1982, "The Meaning and Use of the Area Under a Receiver Operating Characteristic (ROC) Curve.", *Radiology* 143 (1): 29-36. Taking into account the correlation between pixels within the same ROI, the amount of independent benign and malignant samples is conservatively set to the number of benign and malignant ROI's, being 60 and 61, respectively, as not all planes contained both suitable benign and malignant regions. The difference in performance was considered significant for p<0.01.

Figure 6A:
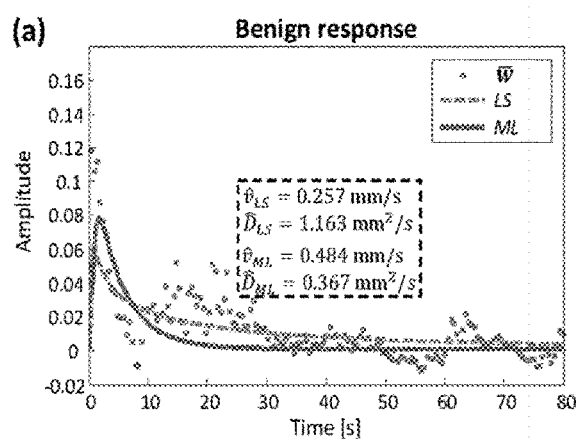
FIGS. 6A and 6B illustrate the difference between Wiener filter estimates in benign and malignant pixels.
Figure 6B:
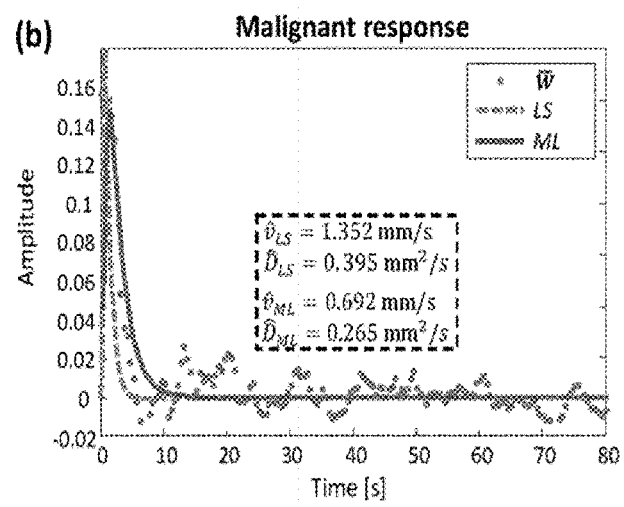

FIGS. 6A and 6B illustrate the difference between Wiener filter estimates in benign and malignant pixels. FIGS. 6A and 6B show the Wiener filter coefficient estimates obtained from a pixel in a benign (FIG. 6a) and a malignant (FIG. 6b) region. The convection-diffusion Green's functions for least squares (LS) and maximum likelihood (ML) parameter estimation are also shown. It has been observed that in this exemplification, the estimated velocities were higher and the dispersion coefficients were lower for malignant pixels.

Figure 7:
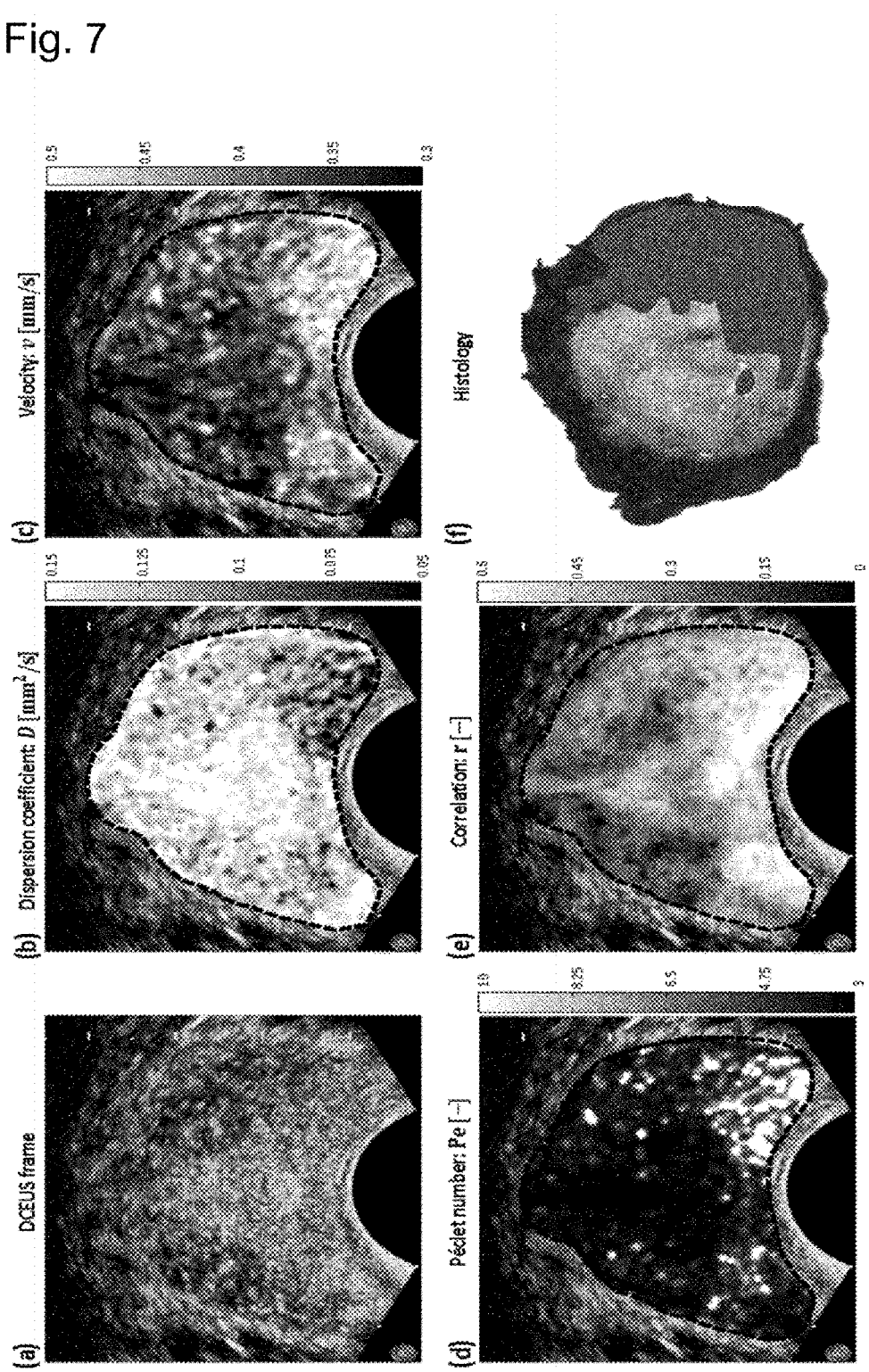
FIG. 7A shows an example of a DCE-US frame.
FIG. 7B shows the estimated dispersion coefficient D.
FIG. 7C the estimated velocity v.
FIG. 7D shows the estimated Péclet number Pé.
FIG. 7E is a map based on the dispersion-related correlation analysis.
FIG. 7F shows a corresponding histology slice.

An example of hemodynamic parametric images obtained by applying the proposed approach, along with the corresponding histology slice, are shown in FIG. 7. FIG. 7A shows an example of a DCE-US frame. The dispersion coefficient D is shown in FIG. 7B and the velocity v is shown in FIG. 7C. FIG. 7D shows the Péclet number Pé. FIG. 7E is a map based on the dispersion-related correlation analysis described in previous work, see Kuenen et al., IEEE Transactions on ultrasonics, ferroelectrics and frequency control, 2013. A corresponding histology slice is shown in FIG. 7F in which two areas 71 and 72 indicate regions two tumor locations. In this case, model parameter estimation is performed using ML.

Although it is not a one-to-one match, the dark area on the right hand side of the dispersion coefficient image, see FIG. 7B, as well as the enhanced bright area in the velocity, see FIG. 7C and Péclet number image, see FIG. 7D qualitatively imply angiogenic vasculature, indicating the tumor's location.

Figure 8:
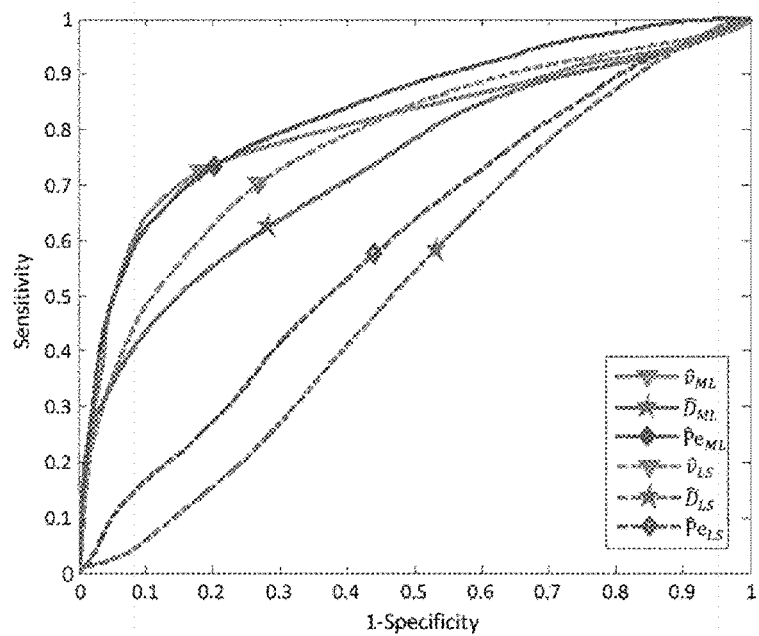
FIG. 8 shows a graph of the Receiver-Operating-Characteristic (ROC) curves for classification of benign and malignant pixels by the estimated dispersion coefficient (D), velocity (v) and Péclet number (Pe), as obtained using Maximum Likelihood (ML) and Least Squares (LS)

FIG. 8 shows a graph of the Receiver-Operating-Characteristic (ROC) curves for classification of benign and malignant pixels by the estimated dispersion coefficient (D), velocity (v) and Péclet number (Pe), as obtained using Maximum Likelihood (ML) and Least Squares (LS). In FIG. 8, the ROC curves for pixel-based classification using the dispersion coefficient, velocity, and Péclet number are given. To compare their performances, the curves when employing ML as well as LS to estimate the model parameters are shown. An overview of these results, including the corresponding PPV, NPV, and the ROC curve areas, is given in Table 1. Table 1 shows classification results based on Pe, v, and D as obtained using Maximum Likelihood (ML) and Least Squares (LS) optimization, compared to the results obtained using the previously developed dispersion-related correlation analysis, see Kuenen et al., IEEE Transactions on ultrasonics, ferroelectrics and frequency control, 2013.

TABLE 2

|  | Parameter | Sensitivity [%] | Specificity [%] | Negative Predictive Value [%] | Negative Predictive Value [%] | ROC curve area |
|---|---|---|---|---|---|---|
| ML | v | 72.5 | 82.1 | 74.9 | 80.2 | 0.807 |
|  | D | 62.5 | 71.8 | 65.7 | 68.9 | 0.733 |
|  | Pe | 73.4 | 79.9 | 75.0 | 78.5 | 0.835 |
| LS | v | 70.2 | 73.3 | 71.1 | 72.4 | 0.777 |
|  | D | 58.3 | 46.9 | 52.9 | 52.3 | 0.521 |
|  | Pe | 57.5 | 56.0 | 56.9 | 56.6 | 0.592 |
| Kuenen, 2013 | r | 64.0 | 74.9 | 64.8 | 74.3 | 0.730 |

Figure 9A:
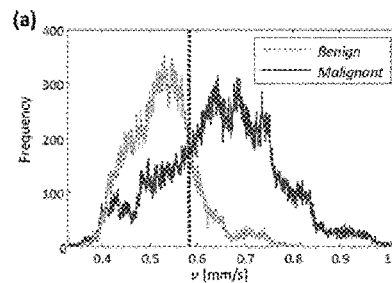
FIGS. 9A and 9B show an indication of the probability distributions of the parameters given the class, histograms of the ML estimates of v and D.
Figure 9B:
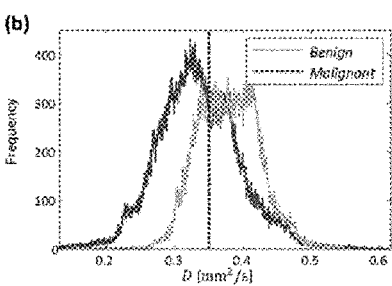

It is shown from Table 1 that using ML instead of LS yielded significantly higher ROC curve areas for the estimation of D (p=0.0024) and Pe (p=0.0001). The improvement with respect to v estimation was not statistically significant (p=0.62). Comparing the ML estimates of v, and D, it has been observed that v yielded a higher sensitivity and specificity than D. Classification using Pe showed the highest ROC curve area, being 0.84. Having an ROC curve area equal to 0.73, the spatial correlation analysis showed a lower performance. To give an indication of the probability distributions of the parameters given the class, histograms of the ML estimates of v and D in the ROI's are shown in FIGS. 9A and 9B. The benign and malignant class means±standard deviations for v were 0.53±0.07 mm/s and 0.65±0.12 mm/s, respectively. For D these values were 0.38±0.045 mm²/s and 0.33±0.059 mm²/s, respectively. It can be observed that for malignant pixels, the underlying contrast agent kinetics tended to be characterized by a higher velocity and a lower dispersion compared to benign pixels.

FIGS. 9A and 9B show the benign and malignant class histograms for the Maximum Likelihood estimates of the velocity (v) and dispersion coefficient (D). The optimal classification thresholds are indicated by a dashed line. A pixel was classified malignant for v >0.583 mm/s, and for D<0.350 mm²/s.

The above described embodiments can be used in a method for e.g. prostate cancer localization based on dynamic contrast enhanced ultrasound (DCE-US) imaging. By combining Wiener system identification and model-based parameter estimation, the proposed embodiments enable local characterization of the hemodynamics described by the dispersion coefficient (D), velocity (v), and Péclet number (Pe). The obtained parameters serve as features that relate to angiogenic activity. Stable estimates of the Wiener filter coefficients may be obtained by adopting an information theoretic criterion, allowing regularized matrix inversion by determining the pure signal subspace from the eigenvalues, without requiring any subjective threshold settings. Next, model-based Least Squares (LS) and Maximum Likelihood (ML) parameter estimators may be derived to estimate the dispersion coefficient and velocity.

A qualitative comparison of the resulting parametric maps exemplified how the dispersion and velocity maps suggested the presence of angiogenic vasculature by showing dark or bright areas, respectively. The Péclet number map qualitatively displays a higher specificity, with bright areas implying angiogenic activity. Set against the corresponding histology slice, these areas indicated the presence of cancer.

A quantitative analysis showed that the ML parameter estimates outperformed the LS estimates in terms of receiver operator characteristic (ROC) curve area at distinguishing benign from malignant pixels. In particular, the estimated dispersion coefficient, and consequently the Péclet number, showed a significantly improved performance. This has been exemplified in FIG. 6, notably for the displayed malignant case. The ML response was typically more similar to the estimated Wiener coefficients. This result was expected, given that the model parameters are derived from it. On the other hand, the LS model parameters are directly derived from the input autocorrelation and output-input cross-correlations to avoid matrix inversion. By comparing the performance of v, D, and Pe, it has been concluded that the highest ROC curve area and the greatest flexibility is obtained for the ML estimate of Pe, having an ROC curve area of 0.84. followed by the ML and LS estimates of v. Although the ML estimate of D performs worse than v, it does show diagnostic value and yields an ROC curve area of 0.73.

The lower dispersion observed in malignant regions may be a result of the tortuous nature of angiogenic neovasculature, limiting the diffusion of contrast agents in the measurement cell. This process is very similar to the diffusion of particles through porous media, where a decrease in macroscopic diffusion owing to irregular geometry of the porous media is predicted. The effective diffusion decreases with increasing tortuosity. Angiogenic vascularity is also characterized by high-velocity arteriovenous shunts, which may cause the observed elevated flow velocities in malignant regions.

Below some embodiments are described that enable velocity vector field imaging and tractography of ultrasound contrast agents in the bloodstream, from DCE-US acquisitions.

According to an embodiment, the method of estimating a velocity of a contrast agent includes estimating a plurality of time-delays (τ) between the temporal evolutions (i.e. the DC's) of contrast agent concentration obtained within the pixels/voxels in the local kernel, and then determining the velocity by mapping the plurality of estimated time-delays to the spatial domain.

The mapping may be obtained by solving a set of equations that describes a relation between time-delays, inter-pixel/voxel distance vectors and a velocity vector. The method may further include the estimation of weights and weighted least squares in order to obtain the minimum mean squared error estimate of the velocity vector. The weights may be unity (all equal to one) or a measure of confidence in the estimated time-delays for each estimated time-delay in the set of equations.

Now an example is given of the above described embodiment wherein several steps I-IV are discussed.

I. A local estimation of the microbubble flow velocity and directionality is obtained by describing the time-intensity relation between specific set of imaging voxels. For 2D datasets, this can be (but is not limited to) the set that is closest to a uniformly spaced circular array of pixels. For 3D datasets, the set can be described by (but is not limited to) the voxels closest to the 20 nodes of a regular dodecahedron with a specific radius.

II. Then, the time delays amongst all the log-compressed time-intensity signals in the set are estimated by determining the peak of their cross-correlations. For the two signals $s_i$ and $s_j$ in voxels i and j, respectively, this can be written as:

$$\hat{\tau}_{i,j} = \underset{\tau}{\mathrm{argmax}} E\{s_i(t)s_j(t-\tau)\}, \qquad (32)$$

with $E\{.\}$ denoting the expectation operator.

III. For the complete set of voxels, the local propagation velocity vector $\vec{v}$ can then be estimated by solving the following linear system of equations:

$$\vec{v}\, Tr = D, \qquad (33)$$

where τ is the vector that contains all the estimated time delays and D is the matrix that describes the inter-voxel distance vectors. This procedure is repeated for all pixels in order to produce a velocity vector field.

3D datasets, having a lower temporal resolution, are up-sampled by a factor 10 to facilitate a more precise time-delay estimate.

Figure 10:
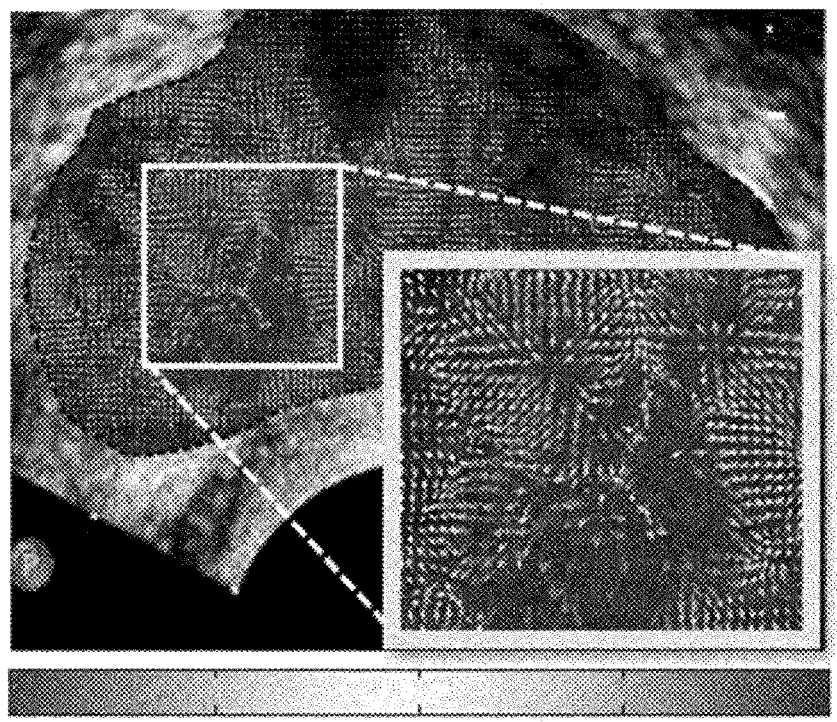
FIG. 10 shows an example of the velocity vector fields derived from 2D DCE-US imaging data.

IV. An example of the above described embodiment applied to 2D DCE-US imaging data is given in FIG. 10 which shows the velocity vector fields derived from 2D DCE-US imaging data. It is noted that preferably the image is a colored image so as to be able to easily recognize different velocities in the image.

According to a further embodiment, the method of estimating includes generating a 2D or 3D representation of ultrasound-contrast-agent trajectories, wherein the representation includes a most likely vascular structure, via a predetermined number of seed particles that are associated with a path within the estimated 2D or 3D velocity vector field. First, a predetermined set of particles at seed points may be initialized and next the ultrasound-contrast-agent trajectories at the seed point may be tracked. Then, for each particle, a propagation direction may be determined based on the velocity vectors and each particle may be moved by a predetermined step size in the projection direction.

In an embodiment, an assessment of vascular features is performed based on the representation of ultrasound-contrast-agent trajectories, wherein the vascular features include representations of Tortuosity, Density, Branching and/or Regularity.

The UCA trajectories (tracts) can be obtained from the velocity fields by solving the following ordinary differential equation:

$$\begin{cases} \partial_t x(t) = \vec{v}[x(t)] \\ x(0) = x_0 \end{cases}, \qquad (34)$$

which describes how, given an initial seeding point $x_0$, a particle moves within the velocity vector field $\vec{v}(x)$.

A fifth-order Dormand-Prince Runge-Kutta method may be employed to solve equation (34). After each tract update, the algorithm evaluates whether one of the stopping criteria has been reached, i.e. if a) the tract is stuck within an integration cell, b) the tract has a velocity magnitude that is smaller than the minimally allowed value, $v_{min}$, or c) the tract has reached the maximum number of allowed vertices. Equation 34 is solved for all said seeding points to generate DCE-US tractograms.

Figure 11:
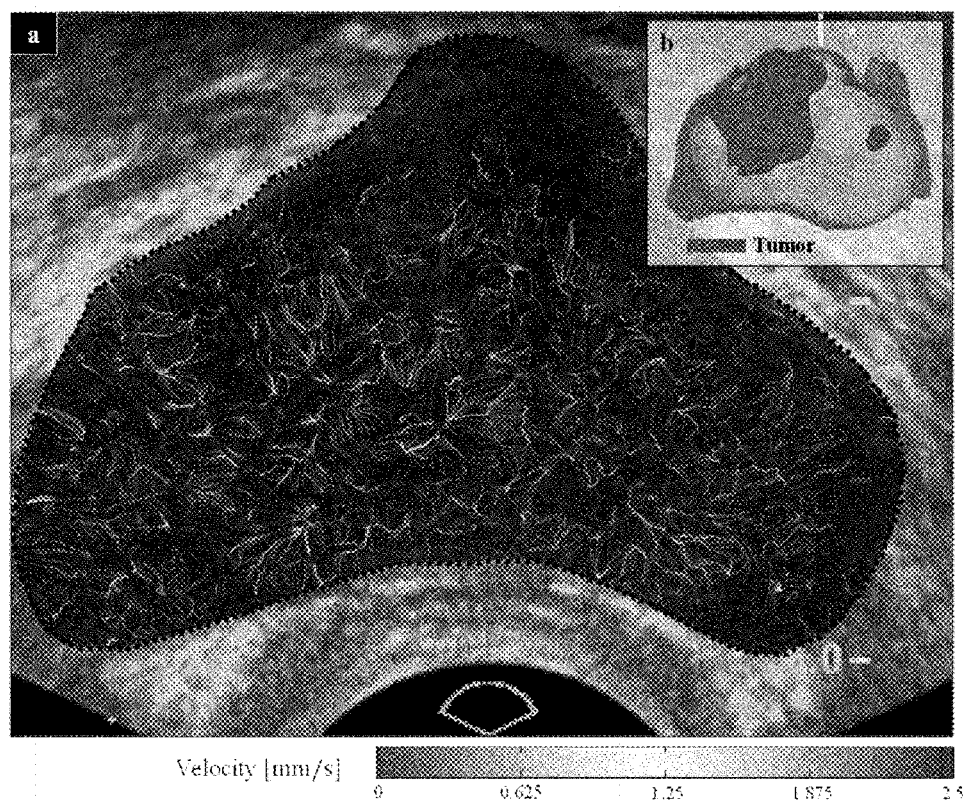
FIG. 11 shows a Contrast ultrasound velocity field tractography (CUVT) applied to in-vivo 2D transrectal dynamic contrast enhanced ultrasound imaging of a prostate.

An example of the above described embodiment applied to 2D DCE-US imaging data is given in FIG. 11. FIG. 11 shows a Contrast ultrasound velocity field tractography (CUVT) applied to in-vivo 2D transrectal dynamic contrast enhanced ultrasound imaging of a prostate. FIG. 11a is CUVT image, velocity values can be color coded from e.g. blue to red. FIG. 11b is a corresponding histology slice.

Figure 12:
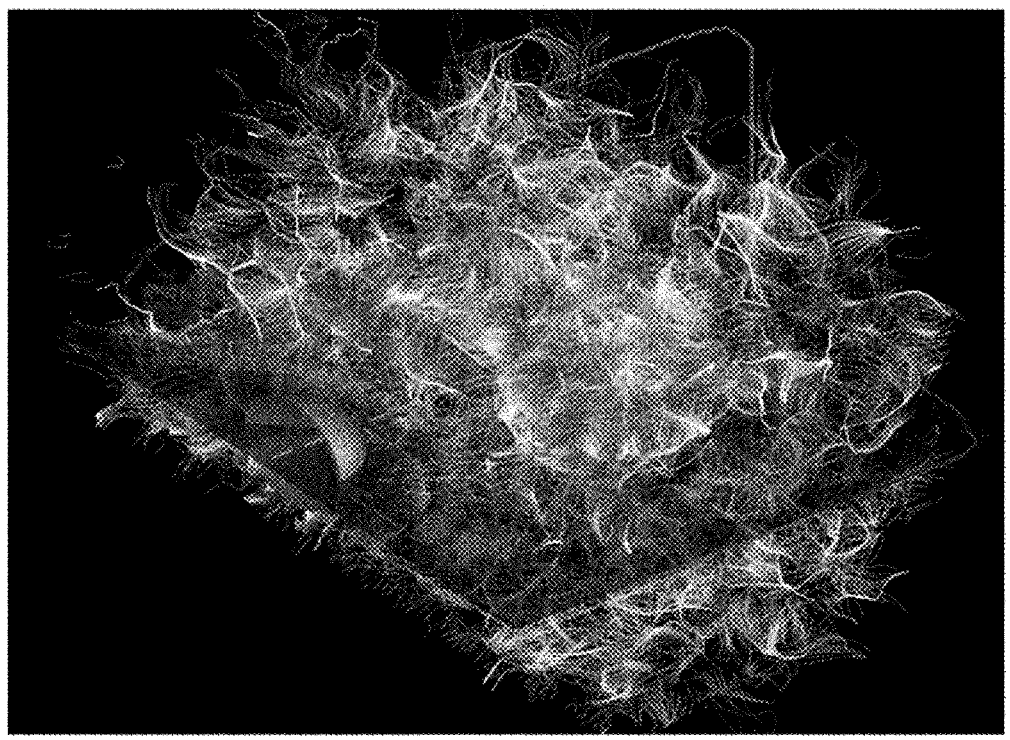
FIG. 12 shows a contrast ultrasound velocity field tractography (CUVT) applied to in-vivo 3D transrectal dynamic contrast enhanced ultrasound imaging of a prostate.

Another example of the above described embodiment applied to 3D DCE-US imaging data is given in FIG. 12. FIG. 12 shows a contrast ultrasound velocity field tractography (CUVT) applied to in-vivo 3D transrectal dynamic contrast enhanced ultrasound imaging of a prostate. Here it is also noted that preferably the output images are color images to facilitate interpretation.

The implementation of the above discussed embodiment can be based on probabilistic streamline tracking, where said seed points will generate a plurality of potential trajectories based on said velocity vector field and a probabilistic model, wherein a figure of likelihood or merit is determined for each potential UCA trajectory.

Figure 13:
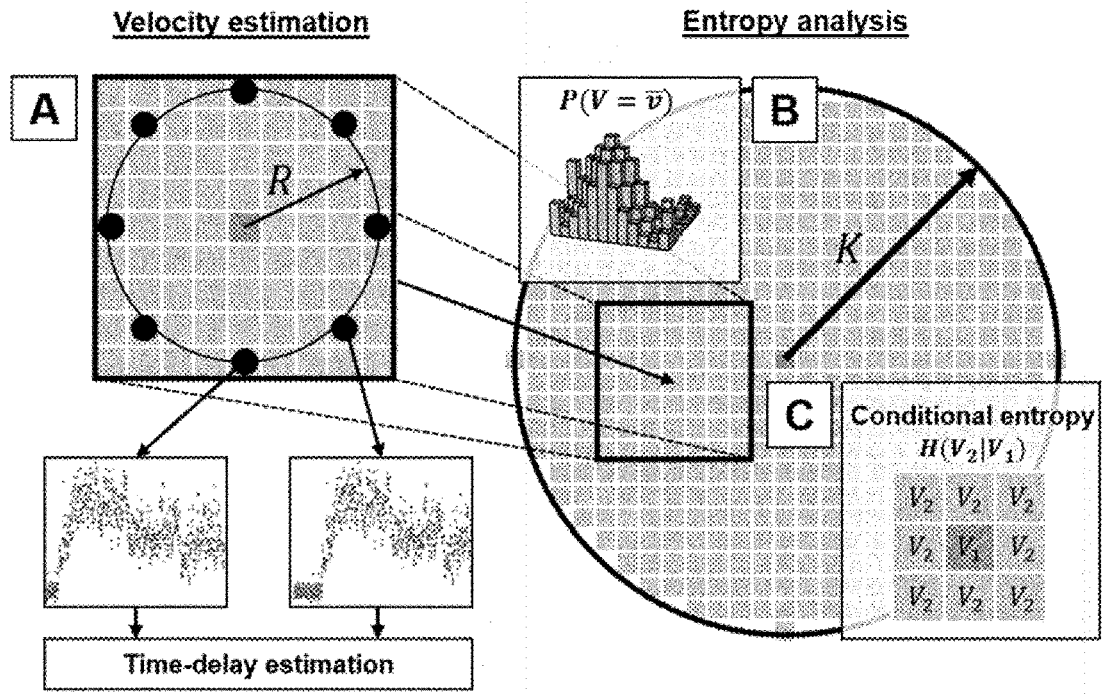
FIGS. 13A-13C show an illustration of the method steps according to a further embodiment.

FIGS. 13A-13C show an illustration of the method steps according to a further embodiment. The method may include the following steps:

I. Based on the velocity vector field data (FIG. 13A), calculate Shannon's entropy as a measure of disorder. To this end, estimate the probability distribution from the velocity vector field data within a kernel (FIG. 13B). Possible estimators include: Histogram estimator, Kernel Density Estimator.

II. Calculate Shannon's conditional entropy as a measure of the predictive value of a velocity vector with respect to its surrounding pixels (FIG. 13C). To this end, estimate the conditional probability mass function of a velocity vector at a certain location, given a neighbouring velocity vector.

III. Repeat this procedure by moving said kernel over the image domain, calculating a value of entropy and conditional entropy for all pixels/voxels of interest, to produce parametric maps.

IV. ROI-based prostate cancer classification results on 24 patients for this embodiment are presented using a Receiver-Operator-Characteristics curve in FIG. 14. The ground truth was based on histology. For comparison, the results for relevant previous methods are also displayed.

Figure 14:
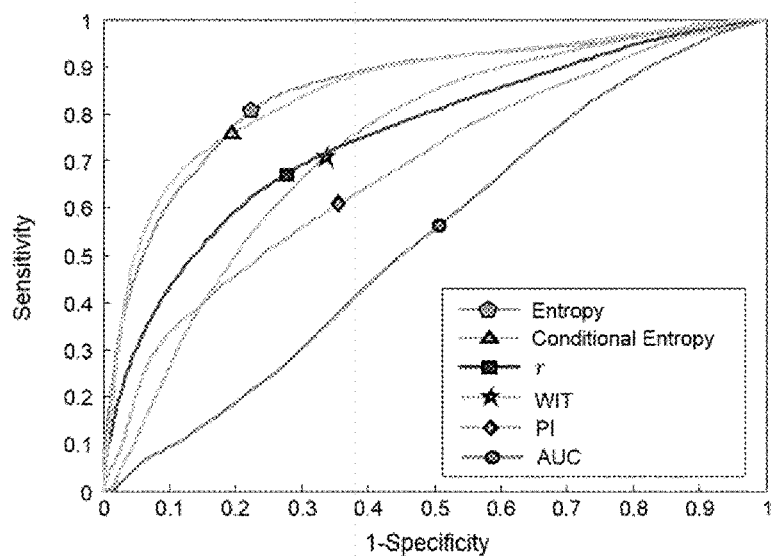
FIG. 14 shows a graph with Receiver-Operator-Characteristic curves for the classification performance of the proposed Entropy and Conditional Entropy based parameters.

FIG. 14 shows a graph with Receiver-Operator-Characteristic curves for the classification performance of the proposed Entropy and Conditional Entropy based parameters, against those obtained with spatiotemporal IDC correlation ($\tau$), wash-in-time (WIT), peak intensity (PI), and the area under the IDC (AUC) as parameters.

Figure 15:
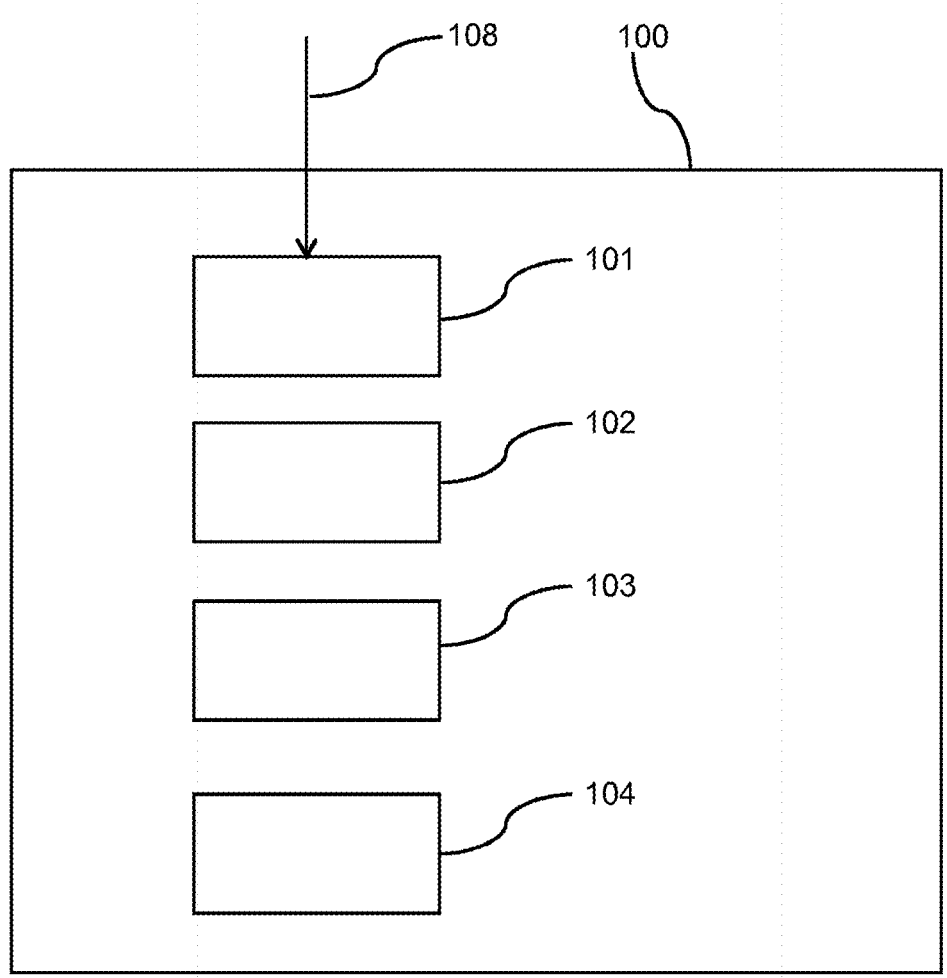
FIG. 15 shows an embodiment of an estimating system 100 for estimating a velocity of a contrast agent.

FIG. 15 shows an embodiment of an estimating system 100 for estimating a velocity of a contrast agent. The system 100 includes an input module 101 for receiving a plurality of video frames 108 that were produced using a dynamic contrast enhanced imaging process, each video frame including a plurality of pixels/voxels.

The system 100 further includes an image processing module 102 configured for:
defining a local kernel, the local kernel including a number of neighboring pixels/voxels;
placing the local kernel at a first location relative to the video frames;
determining indicator-dilution curves for the pixels/voxels in the local kernel using the received plurality of video frames;
comparing the indicator-dilution curves between two of a pair of pixels/voxels for a number of pairs of pixels/voxels within the local kernel to obtain a spatiotemporal dependency of the concentration evolution between the pixels/voxels within the local kernel;
repeating the step of comparing the indicator-dilution curves after having relocated the local kernel, until no relocation of the local kernel is needed.

The system 100 also includes an estimating module 103 for estimating the velocity for at least some of the pixels/voxels of the video frames using the spatiotemporal dependency. The system 100 also includes an output module 104 for rendering the estimated velocity in a 2D or 3D image.

The estimating module may a solving module (not shown) for solving a convection-diffusion model using the plurality of video frames to obtain a measure of the spatiotemporal evolution of the contrast agent concentration.

The system 100 may be implemented in a computer by means of hardware and/or software. The modules 101-104 may be hardware and/or software. The system may include a processor and a memory for storing data and/or computer instruction which when executed on the processor, enable the system to perform the methods as described by the embodiments.

The above has been described with reference to ultrasound technologies, and displayed results relate to prostate cancer. The described method and system may also be applied to other contrast-enhanced imaging technologies. Furthermore, some embodiments may also apply to other types of cancer or diseases with marked angiogenic activity e.g.:
cancer diagnostics by angiogenesis localization with contrast-enhanced imaging (ultrasound, MRI, CT, etc.)
imaging of inflammatory tissue with involved angiogenic activity
image guided targeting of biopsies for cancer diagnosis
image guided targeting of focal cancer treatment
follow-up of cancer therapy.

In the claims, any reference signs placed between parentheses shall not be construed as limiting the claim. Use of the verb "include" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention claimed is:

1. A method of estimating a velocity of a contrast agent, the method comprising:
receiving a plurality of video frames that were produced using a dynamic contrast enhanced imaging process, each video frame comprising a plurality of pixels/voxels;
defining a local kernel, the local kernel including a number of neighboring pixels/voxels;
placing the local kernel at a first location relative to the video frames;
determining indicator-dilution curves for the pixels/voxels in the local kernel using the received plurality of video frames;
comparing the indicator-dilution curves between two of a pair of pixels/voxels for a number of pairs of pixels/voxels within the local kernel to obtain a spatiotemporal dependency of the concentration evolution between the pixels/voxels within the local kernel;
repeating the step of comparing the indicator-dilution curves after having relocated the local kernel, until no relocation of the local kernel is needed;
estimating the velocity for at least some of the pixels/voxels of the video frames using the spatiotemporal dependency; and
rendering the estimated velocity in a 2D or 3D image.

2. The method according to claim 1, wherein the step of estimating the velocity comprises:
determining a convection-diffusion model using the spatiotemporal dependency; and
identifying the convection-diffusion model to obtain the velocity and dispersion values.

3. The method according to claim 2, wherein the method comprises:
determining an indicator-dilution curve for a pixel/voxel located at the center of the local kernel to obtain an input indicator-dilution curve;
defining the indicator-dilution curves of the pixels/voxels of the local kernel as output indicator-dilution curves;
defining Wiener-Hopf equations that describe the relation between the autocorrelation function of the input indicator-dilution curve and the cross-correlation function between the input indicator-dilution curve and output indicator-dilution curves;
solving the Wiener-Hopf equations to obtain Wiener filter coefficients that represent a local channel impulse response, describing the spatiotemporal dependency;
defining the convection-diffusion model in terms of the Wiener filter coefficients;
solving the convection-diffusion model by model fitting the Wiener coefficients to obtain the velocity at at least some of the pixels/voxels.

4. The method according to claim 2, wherein the method comprises:
converting the convection-diffusion model into a discrete Markov process, wherein a temporal prediction of the process states, being the contrast agent concentration over space, are defined in terms of current process states, a time step, and process model parameters being the velocity and the dispersion;
augmenting the state vector with the velocity and dispersion;
estimating the process state by filtering the indicator-dilution curves for all the pixels/voxels in the local kernel.

5. The method according to claim 2, wherein the method further comprises:
adding one or more compartments to the convection-diffusion model to be identified to obtain a compartment model; and
modeling extravasation kinetics of extravascular agents and the binding kinetics of targeted agents using the compartment model.

6. The method according to claim 2, wherein the method further comprises:
combining the estimated velocity and the dispersion values into a quantity by arithmetic operations or machine learning algorithms; and
generating the 2D or 3D image using the quantity.

7. The method according to claim 6, wherein the method further comprises:
estimating the Péclet number for at least some of the pixels/voxels using the formula:

$$Pé = L*(v/D)$$

wherein Pé is the Péclet number, L is a characteristic length, v is the velocity and D is the dispersion value.

8. The metod according to claim 1, the method further comprising:
estimating a plurality of time-delays ($\tau$) between the temporal evolutions of contrast agent concentration obtained within the pixels/voxels in the local kernel, and
determining the velocity by mapping the plurality of estimated time-delays to the spatial domain.

9. The method according to claim 8, wherein the mapping is obtained by solving a set of equations that describes a relation between time-delays, inter-pixel/voxel distance vectors and a velocity vector.

10. The method according to claim 9, the method further comprising:
estimating weights and weighted least squares.

11. The method according to claim 10, wherein the weights are one of the following:
unity, and
a measure of confidence in the estimated time-delays.

12. The method according to claim 1, wherein the method further comprises:
impulse response identification amongst a set of indicator dilution curves within the local kernel to obtain time parameters and a mean transit time value ($\mu$).

13. The method according to claim 12, wherein the impulse response identification is performed using a parametric model including:
Local Density Random Walk model;
Lognormal model;
Gamma-variate model;
Erlang function, or
Lagged Normal function.

14. The method according to claim 1, the method further comprising characterization of a velocity vector field, wherein the characterization is performed using one of the following methods:
statistical characterization by calculating the velocity field's entropy; and
pattern recognition with machine learning.

15. The method according to claim 1, the method further comprising:
generating a 2D or 3D representation of ultrasound-contrast-agent trajectories, the representation including a most likely vascular structure, via a predetermined number of seed particles that are associated with a path within the estimated 2 or 3-dimensional velocity vector field.

16. The method according to claim 15, wherein the generating a 2D or 3D representation comprises:
initializing a predetermined set of particles at seed points;
tracking the ultrasound-contrast-agent trajectories at the seed point; and
determining, for each particle, a propagation direction based on the velocity vectors and moving each particle by a predetermined step size in the projection direction.

17. The method according to claim 15, the method further comprising an assessment of vascular features based on the representation of ultrasound-contrast-agent trajectories, wherein the vascular features comprise representations of at least one of Tortuosity, Density, Branching, Fractality and Regularity.

18. An estimating system for estimating a velocity of a contrast agent, the system comprising:
an input module for receiving a plurality of video frames that were produced using a dynamic contrast enhanced imaging process, each video frame comprising a plurality of pixels/voxels;
an image processing module for:
defining a local kernel, the local kernel comprising a number of neighboring pixels/voxels;
placing the local kernel at a first location relative to the video frames;
determining indicator-dilution curves for the pixels/voxels in the local kernel using the received plurality of video frames;
comparing the indicator-dilution curves between two of a pair of pixels/voxels for a number of pairs of pixels/voxels within the local kernel to obtain a spatiotemporal dependency of the concentration evolution between the pixels/voxels within the local kernel; and
repeating the step of comparing the indicator-dilution curves after having relocated the local kernel, until no relocation of the local kernel is needed;
an estimating module for estimating the velocity for at least some of the pixels/voxels of the video frames using the spatiotemporal dependency; and
an output module for rendering the estimated velocity in a 2D or 3D image.

19. The estimating system according to claim 18, the system further comprising a solving module for solving a convection-diffusion model using the plurality of video frames to obtain a measure of the spatiotemporal evolution of the contrast agent concentration.

20. The estimating system according to claim 18, the system further comprising:
an estimator configured for estimating a plurality of time-delays ($\tau$) between the temporal evolutions of contrast agent concentration obtained within the pixels/voxels in the local kernel; and a velocity determinator configured for determining the velocity by mapping the plurality of estimated time-delays to the spatial domain.

21. The estimating system according to claim 18, the system further comprising:

an identification module configured for impulse response identification amongst a set of indicator dilution curves within the local kernel to obtain time parameters and a mean transit time value ($\mu$).

22. The estimating system according to claim 18, the system further comprising a module configured for determination of ultrasound-contrast-agent trajectories based on the velocity.

* * * * *